(12) United States Patent
Nottelet et al.

(10) Patent No.: US 11,383,008 B2
(45) Date of Patent: Jul. 12, 2022

(54) SURFACE-MODIFIED POLYMERIC SUBSTRATES GRAFTED WITH A PROPERTIES-IMPARTING COMPOUND USING CLIP CHEMISTRY

(71) Applicants: Centre National de la Recherche Scientifique (CNRS), Paris (FR); Universite de Montpellier, Montpellier (FR); Ecole Nationale Superieure de Chimie de Montpellier—ENSCM, Montpellier (FR)

(72) Inventors: Benjamin Nottelet, Montpellier (FR); Anita Schulz épouse Luxenhofer, Wuerzburg (DE); Jean Coudane, Lattes (FR)

(73) Assignees: Centre National de la Recherche Scientifique (CNRS) (FR); Universite De Montpellier; Ecole Nationale Supérieure de Chimie de Montpellier—ENSCM

( * ) Notice: Subject to any disclaimer, the term of this patent is extended or adjusted under 35 U.S.C. 154(b) by 36 days.

(21) Appl. No.: 16/312,594

(22) PCT Filed: Jun. 23, 2017

(86) PCT No.: PCT/EP2017/065596
§ 371 (c)(1),
(2) Date: Dec. 21, 2018

(87) PCT Pub. No.: WO2017/220804
PCT Pub. Date: Dec. 28, 2017

(65) Prior Publication Data
US 2019/0247551 A1 Aug. 15, 2019

(30) Foreign Application Priority Data
Jun. 24, 2016 (WO) ................. PCT/IB2016/001131

(51) Int. Cl.
*A61K 31/14* (2006.01)
*A61L 31/14* (2006.01)
*A61L 27/34* (2006.01)
*A61K 49/12* (2006.01)
*A61L 31/10* (2006.01)
*C08G 73/06* (2006.01)
*C08G 81/00* (2006.01)

(52) U.S. Cl.
CPC .............. *A61L 31/14* (2013.01); *A61K 49/12* (2013.01); *A61L 27/34* (2013.01); *A61L 31/10* (2013.01); *C08G 73/06* (2013.01); *C08G 81/00* (2013.01); *A61L 2300/404* (2013.01); *A61L 2300/442* (2013.01); *A61L 2420/02* (2013.01)

(58) Field of Classification Search
CPC .......... A61L 31/14; A61L 27/34; A61L 31/10; A61L 2300/442; A61L 2300/404; A61L 2420/02; C08G 81/00; C08G 73/06; A61K 49/12
See application file for complete search history.

(56) References Cited

U.S. PATENT DOCUMENTS

| | | | |
|---|---|---|---|
| 6,090,995 | A | 7/2000 | Reich et al. |
| 2010/0028559 | A1 | 2/2010 | Yan et al. |
| 2010/0152708 | A1 | 6/2010 | Li et al. |
| 2012/0178872 | A1 | 7/2012 | Blanquer et al. |
| 2014/0302324 | A1 | 10/2014 | Coudane et al. |

FOREIGN PATENT DOCUMENTS

| | | | |
|---|---|---|---|
| EP | 0397130 | A2 | 11/1990 |
| WO | 9000887 | A1 | 2/1990 |
| WO | 9103990 | A1 | 4/1991 |
| WO | 9822542 | A2 | 5/1998 |
| WO | 2011004332 | A1 | 1/2011 |
| WO | 2013084204 | A1 | 6/2013 |

OTHER PUBLICATIONS

International Search Report for PCT/EP2017/065596 dated Sep. 29, 2017.
Balazs DJ, Triandafillu K, Wood P, Chevolot Y, Van Delden C, Harms H, Hohenstein C, Mathieu HJ. Inhibition of bacterial adhesion on PVC endotracheal tubes by RF-oxygen glow discharge, sodium hydroxide and silver nitrate treatments. Biomaterials. May 1, 2004;25(11):2139-51.
Blanquer S, Tailhades J, Darcos V, Amblard M, Martinez J, Nottelet B, Coudane J. Easy synthesis and ring-opening polymerization of 5-Z-amino-d-valerolactone: New degradable amino-functionalized (Co) polyesters. Journal of Polymer Science Part A: Polymer Chemistry. Dec. 15, 2010;48(24):5891-8.
Campoccia D, Montanaro L, Arciola CR. A review of the biomaterials technologies for infection-resistant surfaces. Biomaterials. Nov. 1, 2013;34(34):8533-54.

(Continued)

*Primary Examiner* — Robert S Cabral
(74) *Attorney, Agent, or Firm* — Lerner, David, Littenberg, Krumholz & Mentlik, LLP

(57) ABSTRACT

The present invention relates to an efficient method for grafting a properties-imparting compound onto a polymeric substrate containing carbon-hydrogen (C—H) bonds using clip chemistry. The method of the invention includes coating the substrate with the properties-imparting compound and irradiating it with a reactive light source, and repeating this sequence at least once. The present invention further relates to surface-modified polymeric substrates grafted with a properties-imparting compound, in particular obtained with the method of the invention, medical devices comprising same, and non-medical of said surface-modified polymeric substrates.

14 Claims, 9 Drawing Sheets

(56) References Cited

OTHER PUBLICATIONS

Coll Ferrer MC, Yang S, Eckmann DM, Composto RJ. Creating biomimetic polymeric surfaces by photochemical attachment and patterning of dextran. Langmuir. Aug. 16, 2010;26(17):14126-34.

Kenawy ER, Worley SD, Broughton R. The chemistry and applications of antimicrobial polymers: a state-of-the-art review. Biomacromolecules. May 14, 2007;8(5):1359-84.

El Habnouni S, Lavigne JP, Darcos V, Porsio B, Garric X, Coudane J, Nottelet B. Toward potent antibiofilm degradable medical devices: A generic method for the antibacterial surface modification of polylactide. Acta biomaterialia. Aug. 1, 2013;9(8):7709-18.

El Habnouni S, Nottelet B, Darcos V, Porsio B, Lemaire L, Franconi F, Garric X, Coudane J. MRI-Visible poly (e-caprolactone) with controlled contrast agent ratios for enhanced visualization in temporary imaging applications. Biomacromolecules. Sep. 17, 2013;14(10):3626-34.

Leroy A, Nottelet B, Bony C, Pinese C, Charlot B, Garric X, Noël D, Coudane J. PLA-poloxamer/poloxamine copolymers for ligament tissue engineering: sound macromolecular design for degradable scaffolds and MSC differentiation. Biomaterials science. 2015;3(4):617-26.

Leroy A, Pinese C, Bony C, Garric X, Noël D, Nottelet B, Coudane J. Investigation on the properties of linear PLA-poloxamer and star PLA-poloxamine copolymers for temporary biomedical applications. Materials Science and Engineering: C. Oct. 1, 2013;33(7):4133-9.

Morille M, Van-Thanh T, Garric X, Cayon J, Coudane J, Noël D, Venier-Julienne MC, Montero-Menei CN. New PLGA-P188-PLGA matrix enhances TGF-β3 release from pharmacologically active microcarriers and promotes chondrogenesis of mesenchymal stem cells. Journal of controlled release. Aug. 28, 2013;170(1):99-110.

Nottelet B, Patterer M, François B, Schott MA, Domurado M, Garric X, Domurado D, Coudane J. Nanoaggregates of biodegradable amphiphilic random polycations for delivering water-insoluble drugs. Biomacromolecules. Apr. 9, 2012;(5):1544-53.

Samuel R, Girard E, Chagnon G, Dejean S, Favier D, Coudane J, Nottelet B. Radiopaque poly (e-caprolactone) as additive for X-ray imaging of temporary implantable medical devices. Rsc Advances. 2015;5(102):84125-33.

Sardo C, Nottelet B, Triolo D, Giammona G, Garric X, Lavigne JP, Cavallaro G, Coudane J. When functionalization of PLA surfaces meets Thiol-Yne photochemistry: case study with antibacterial polyaspartamide derivatives. Biomacromolecules. Oct. 28, 2014;15(11):4351-62.

Timofeeva L, Kleshcheva N. Antimicrobial polymers: mechanism of action, factors of activity, and applications. Applied microbiology and biotechnology. Feb. 1, 2011;89(3):475-92.

Younis M, Darcos V, Paniagua C, Ronjat P, Lemaire L, Nottelet B, Garric X, Bakkour Y, El Nakat JH, Coudane J. MRI-visible polymer based on poly (methyl methacrylate) for imaging applications. RSC Advances. 2016;6(7):5754-60.

A:

SURFACE-MODIFIED POLYMERIC SUBSTRATES GRAFTED WITH A PROPERTIES-IMPARTING COMPOUND USING CLIP CHEMISTRY

CROSS-REFERENCE TO RELATED APPLICATIONS

The present application is a national phase entry under 35 U.S.C. § 371 of International Application No. PCT/EP2017/065596, filed Jun. 23, 2017, which claims priority from PCT/IB2016/001131, filed Jun. 24, 2016, all of which are incorporated herein by reference.

The present invention relates to surface-modified polymeric substrates grafted with a properties-imparting compound, medical devices comprising same, and a method for grafting a polymeric substrate.

BACKGROUND ART

Medical devices are an integral part of modern medicine. About half a billion devices are used per year.

Recently, smart medical devices have been developed, wherein the surface is modified to render them multifunctional.

For instance, some medical devices exhibit a surface modified to render them useful in medical imaging. Such medical devices are for instance described in applications WO 2011/004332 and WO 2013/084204. However, in WO 2011/004332 and WO 2013/084204, the medical device is coated with a polymer, which is not covalently bound to the substrate, so that undesired leaching phenomena may occur.

Also, a wide-spread issue linked to the use of implants remains bacterial infection (e.g. catheter induced urinary tract infection in critically ill patients). It is indeed assumed that about 45% of all nosocomial infections are caused by implanted devices.

In contrast to non-implant related infections, only a few bacteria adhering to the implant surface are sufficient to trigger an infection. Once adhered to the surface, changes in the metabolism and phenotype of the bacteria protect them from the typically compromised immune response and render them resistant to most antimicrobial agents. Moreover, bacteria induce formation of a biofilm—a matrix of proteins, polysaccharides and extracellular DNA—said biofilm being a major impediment in the treatment of implant-related infections. To effectively cure the infection, the implant most of the time has to be removed, causing further pain and distress for the patient. This is not only a medical predicament: in the U.S. alone, the cost for additional hospitalization and treatment is estimated to be over $3 billion per year.

While a sterile environment keeps the risk of infection low, most contaminations still occur peri-operatively and often the pathogen is introduced by the patient himself. Therefore, considerable effort has been made to generate new bioactive antibacterial surfaces in the last decades. Most of these biomaterials contain either silver or antimicrobials—often embedded in surface coatings—as well as positively charged quaternary ammonium compounds and polycations which act as bactericidals, and are immobilized onto the surface.

Besides bioactive surfaces which kill bacteria, biopassive antifouling modifications which impede protein and bacteria adhesion and thus biofilm formation have been studied. Hydrophilic polymers with antifouling properties such as polyethylene glycol (PEG) are commonly used for this strategy. High coverage of the surface is crucial to prevent uncontrolled adhesion of proteins and bacteria.

Two main methods are used to covalently attach polymers to the surface. While "grafting onto"—the attachment of the polymer chain onto the surface—allows better control and characterization of the polymer, the "grafting from" method, where the polymer is directly synthesized on the surface, often yields higher grafting density, but is limited in its chemical variety.

"Grafting onto" methods were thus developed, which would be flexible, easy to carry out and would be compatible with a wide variety of chemical compounds and implantable devices, which are most of the time made of a biocompatible polymeric material.

In this regard, clip chemistry arose as a technique of choice, as it is compatible with a wide variety of chemical entities, and requires only the material to be grafted to contain CH bonds, which is the case of most polymeric materials.

Clip chemistry consists of a radical insertion of a nitrene radical into a C—H bond, wherein the nitrene radical is preferably generated by irradiation (preferably with light) of an aryl-azide derivative (Ar—$N_3$). Upon irradiation, the aryl-azide decomposes to yield the nitrene radical (Ar—N°), which then reacts with a C—H bond to form a covalent carbon-nitrogen bond between the surface of the substrate and the compounds, as depicted in FIG. 1.

For instance, patent applications WO 90/00887, WO 98/22542, U.S. Pat. No. 6,090,995 or EP 0 397 130 disclose a clip chemistry based direct as well as indirect "grafting onto" method, creating covalent bonds between a hydrophilic polymer and the polymeric implantable device.

Using a similar method, Ferrer et al. (Langmuir 2010, 26(17). 14129-14134) disclose a process for grafting Dextran on the surface of polymeric substrate (polyurethane or polystyrene), using a "clip" reaction between said polymeric substrate and a modified dextran polymer comprising at least one aryl-azide group. However, the method of Ferrer et al. includes a pre-treatment step of the substrate, namely plasma oxidation. Also, the Dextran polymers of Ferrer et al. are "random" polymers as far as the distribution of the $N_3$ functions is concerned.

The methods of the prior art are not satisfactory because most methods require pre-functionalization of the surface to be modified, so as to ensure efficient grafting in particular with acceptable grafting rates.

There thus remains a need for providing a clip chemistry based direct "grafting onto" method which would be efficient and easy to carry out for grafting polymers as well as small molecules onto polymeric substrates, thus efficiently leading to novel multifunctional implantable as well as non-implantable polymer substrates and devices. In addition, the surface-modified substrate thus obtained should be stable and keep its properties over time, i.e. it is desirable that the grafted properties-imparted compound does not degrade or leach over time.

SUMMARY OF THE INVENTION

To address this technical problem, the Inventors have designed a method for grafting a polymeric substrates containing carbon-hydrogen (C—H) bonds with a properties-imparting compound comprising an aryl-azide moiety, by coating the substrate with said properties-imparting compound and irradiating it for a time of less than 30 minutes, and repeating this sequence of steps at least once.

Indeed, carrying out this sequence of steps only once does not result in an efficient grafting of the properties-imparting compound. The Inventors have observed that it is necessary to carry out the sequence several times. In this regard, simply increasing the time of irradiation only increases the degradation of the aryl-azide containing properties-imparting compound, but does not improve the grafting rate. Only repeating of the sequence with a short irradiation time leads to satisfactorily stable grafted substrates.

In contrast with the prior art, the method of the invention may be carried out directly on the polymeric substrate without any prior treatment step. In other words, the surface of the polymeric substrate does not need activating. In particular, the surface of the polymeric substrate does not need oxidizing.

In addition, when the properties-imparting compounds are polymeric, the Inventors have observed that more reliable and reproducible grafting is obtained with a block- or a gradient copolymer with a block or region rich in repeated units containing an aryl-azide moiety, as compared with a simple chain-end aryl-azide containing copolymer.

Therefore, in a first aspect, the invention relates to a method for grafting a properties-imparting compound onto a polymeric substrate containing carbon-hydrogen (C—H) bonds, said method comprising:
a) providing a substrate;
b) coating the substrate with a properties-imparting compound comprising a photoactive aryl-azide moiety of formula (I):

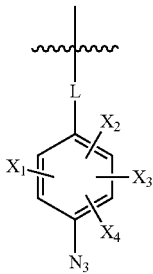

(I)

with $X_1$, $X_2$, $X_3$ and $X_4$ independently representing a hydrogen or a fluorine atom, a $C_1$-$C_6$ alkyl group, $NO_2$ or OH, and L representing NH, —C(O)O—, —S—, —C(O)NH—, —NHC(O)—, —OC(O)—, —NHC(O)NH—, —NHC(S)NH—, —C(O)NRC(O)— with R representing a $C_1$-$C_6$alkyl or triazolyl,
so as to obtain a homogeneous dry layer of said properties-imparting compound coated on at least part of the substrate, and to bring said aryl-azide moiety of formula (I) into covalent bonding proximity with the carbon-hydrogen bonds of the substrate;
c) irradiating the coated substrate with a reactive light source, for a time $t_1$ sufficient to form nitrenes that undergo insertion reactions into carbon-hydrogen bonds of the substrate, $t_1$ being equal to or less than 30 minutes, thereby yielding a grafted polymeric substrate;
d) optionally washing the obtained grafted polymeric substrate;
e) repeating steps b), c) and optionally d) at least once; and
f) optionally drying the grafted substrate obtained at the end of step e).

In another aspect, the invention relates to a surface-modified polymeric substrate, advantageously a surface-modified polymeric implantable substrate obtainable by the process of the invention.

In yet another aspect, the invention concerns a surface-modified polymeric implantable substrate grafted with a properties-imparting compound through the nitrogen atom of an aryl-amino moiety of formula (VI):

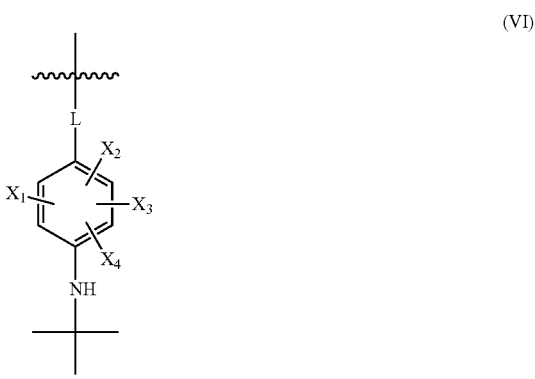

(VI)

with $X_1$, $X_2$, $X_3$ and $X_4$ independently representing a hydrogen or a fluorine atom, a $C_1$-$C_6$ alkyl group, $NO_2$ or OH, and L representing NH, —C(O)O—, —S—, —C(O)NH—, —NHC(O)—, —OC(O)—, —NHC(O)NH—, —NHC(S)NH—, —C(O)NRC(O)— with R representing a $C_1$-$C_6$alkyl or triazolyl,
said properties-imparting compound providing anti-fouling properties, antibacterial properties, or rendering the substrate radio-opaque or visible in medical imaging,
provided that when said properties-imparting compound is a polymer, it is a block- or gradient-copolymer with a block or a region rich in repeated units A, said repeated units A comprising the aryl-amino moiety of formula (VI) as defined above with the nitrogen atom covalently bound to the surface of the surface-modified substrate.

In another aspect, the invention concerns a medical device comprising a surface-modified polymeric (preferably implantable) substrate of the invention.

Definitions

As used herein, an "implantable" polymeric substrate is understood as a polymeric substrate which is meant to be placed inside or on the surface of the body of a patient. It should thus be compatible with a medical use. In particular, it should not be toxic to the body and should not interfere in any detrimental way with the health of the implanted patient. An implantable polymeric substrate should also minimize the risks of rejection by the implanted host.

As used herein, "biocompatible" qualifies a substrate which is suited for implantation, and which undergoes biointegration or disintegration in the body of the implanted patient, depending on its purpose.

As used herein, a rest R represented as

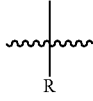

means that the rest R is linked to the rest of the molecule through the bond

As used herein, a rest R—NH represented as

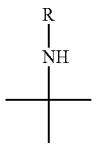

means that the rest is covalently linked to the polymeric substrate through the vertical bond

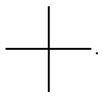

The horizontal line represents the surface of the substrate.

As used herein, the "bonding proximity" is understood as a distance which allows formation of a covalent bond between the reagents, in particular upon irradiation.

In the present invention, IR stands for infrared.

In the present invention, MRI stands for magnetic resonance imaging.

As used herein, a "radio-opaque" compound is a compound that is visible in X-ray imaging, for instance in PET (positron emission tomography).

As used herein, an "antifouling" agent prevents the adhesion of organisms on a synthetic surface. In particular, an antifouling agent prevents the adhesion of bacteria, and in particular prevents the formation of the biofilm, a matrix containing in particular proteins, polysaccharides and extracellular DNA, and bacteria.

As used herein, an "antibacterial agent" is understood as an agent which destroys bacteria or suppresses their growth or their ability to reproduce.

As used herein, an "indirect grafting" method requires first to functionalize the surface of the substrate by grafting a low molecular weight molecule, which serves as an anchor for bonding the properties-imparting compound. Such indirect grafting method is for instance disclosed in patent application US 2010/0028559, which involves first grafting a coupling compound comprising an aryl-azide moiety, which will then undergo a clip chemistry reaction to introduce the properties-imparting compound.

In contrast, a "direct grafting" method, as used herein, refers to a method wherein the properties-imparting compound is grafted directly onto the surface of the substrate, without intermediate molecule serving as an anchoring point for covalently binding the properties-imparting compound. In other words, in a material obtained through a direct grafting process, there is no intermediate molecule between the material surface and the properties-imparting compound. In the present invention, as the properties-imparting compound is grafted thanks to a clip chemistry reaction, it is directly linked to the substrate via a C—NH bond.

As used herein, a "copolymer" is understood as a polymer containing several different repeated units, i.e. at least two different repeated units. A copolymer may be a random copolymer, a block copolymer or a gradient copolymer.

As used herein, a "block copolymer" is understood as a copolymer containing a sequence of different blocks, each containing only one repeated unit. A block copolymer is a single molecule, so that each block is covalently linked to the next block through a covalent bond. For instance, a block copolymer of repeated units A, B and C may have the following structure: AAAAAAAAAABBBBBBBBBCCCCCCCC-CAAAAAAAAACCCCCCCCCBBBBBBBBB.

As used herein, a "gradient copolymer" is understood as copolymers exhibiting a gradual change in monomer composition from predominantly one species to predominantly the other. This is in contrast with block co-polymers, which have an abrupt change in composition As used herein, the term "poloxamer" refers to a tri-block copolymer comprising or consisting of a central polyoxypropylene chain (also called polypropylene oxide, PPO) grafted on either side by a chain of polyoxyethylene (also known as polyethylene oxide, POE). Poloxamers thus comprise a central hydrophobic chain of poly(propylene oxide) surrounded by two hydrophilic chains of poly(ethylene oxide) (PEO-PPO-PEO block copolymer). Poloxamers are generally designated by the letter "P" (for poloxamer) followed by three digits: the first two numbers multiplied by 100 gives the molecular weight of the polyoxypropylene heart, and the last digit multiplied by 10 gives the percentage of content polyoxethylene. For example, P407 (also known as Pluronic® F127) is a poloxamer including a polyoxypropylene heart with a molecular weight of 4000 g/mol and a polyoxyethylene content of 70%.

In the present invention, PEG stands for polyethylene glycol.

In the present invention, PCL stands for polycaprolactone.

In the present invention, a "(meth)acrylate" (or "(meth) acrylic") unit encompasses acrylate (or acrylic) units as well as methacrylate (or methacrylic) units. In particular, a (meth) acrylic group is a $CH_2=C(R)C(O)O(CH_2)_q—$ or a $CH_2=C(R)C(O)O(CH_2)_qO—$ group, wherein R typically represents H or $CH_3$, and q is preferably an integer of between 0 and 15, such as between 3 and 8. Preferred examples of (meth) acrylic groups are $CH_2=CH—C(O)O—CH_2CH_2—$, $CH_2=C(CH_3)—C(O)O—CH_2CH_2—$, $CH_2=CH—C(O)O—CH_2CH_2O—$, and $CH_2=C(CH_3)—C(O)O—CH_2CH_2O—$.

As used herein, a vinylic group is a group (such as a ($C_2$-$C_6$)alkenyl) comprising a terminal double bond. Preferably, the vinylic group of the invention comprises only one double bond. Typically, in the present invention, the vinylic group is of the formula $CH_2=CH—(C_1$-$C_4)$alkyl, or $CH_2=C(CH_3)—(C_1$-$C_4)$alkyl. Examples of vinylic groups are $CH_2=CH—$, $CH_2=CH—CH_2—$ and $CH_2=CH—CH_2—CH_2—$ groups, preferably $CH_2=CH—$.

As used herein, the term "($C_1$-$C_6$)alkyl" refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like. The term "aryl", as used in the present invention, refers to an aromatic group comprising preferably 5 to 10 carbon atoms. The aryl group of the invention may be monocyclic or comprise fused rings. Examples of aryl groups are phenyl or naphtyl groups. Advantageously, it will be a phenyl group.

The term "heteroaryl", as used in the present invention, refers to a 5- to 10-membered aromatic group comprising preferably 1 to 3 heteroatoms selected from N, O or S. The heteroaryl group of the invention may be monocyclic or comprise fused rings. Examples of heteroaryl groups are furanyl, thiopenyl, pyrrolyl, pyridinyl, indolyl.

As used herein, a Huysgens reaction is a 1,3-dipolar addition between a triple bond and an azide group. A Huysgens reaction is also known as "click chemistry", and is usually obtained through heating. It may be catalyzed by copper catalysts. Such reactions are well-known in the art and the skilled artisan will easily implement a Huysgens reaction.

As used herein, a "propargyl group" is understood as a group of formula $HC{\equiv}C-CH_2-$.

The term "amino acid" as used in the present invention refers to natural α-amino acids (e.g. Alanine (Ala), Arginine (Arg), Asparagine (Asn), Aspartic acid (Asp), Cysteine (Cys), Glutamine (Glln), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val)) in the D or L form, as well as non-natural amino acid (e.g β-alanine, allylglycine, tert-leucine, 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxyilic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2S)-2-aminocyclopentanecarboxylic acid, (IR,2S)-2-aminocyclopentanecarboxyilic acid, 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphtoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-aminopyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine acid, γ-carboxyglutamate, β-cyclohexylalanine, citrulline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, nicopetic acid, norleucine, norvaline, octahydroindole-2-carboxylic acid, ornithine, penicillamine, phenylglycine, 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, statines, tetrahydroisoquinoline-1-carboxylic acid, 1,2,3,4-tetrahydroisoquinoline-3-carboxylic acid, or tranexamic acid). Preferably, it will be a natural or non-natural α-amino acid and preferably a natural α-amino acid.

The term "peptide" as used in the present invention refers to a chain comprising 2 to 25 amino acids as defined above (and preferably natural α-amino acid) bound together by means of peptide bonds (i.e. amide function).

For the purpose of the invention, the term "pharmaceutically acceptable" is intended to refer to what is useful to the preparation of a pharmaceutical composition, and what is generally safe and non toxic, for a pharmaceutical use.

As used herein, a pharmaceutically acceptable anion is in particular selected from inorganic anions such as chloride, bromide, sulfate, nitrate, phosphate, or organic anions such as acetate, benzenesulfonate, fumarate, glucoheptonate, gluconate, glutamate, glycolate, hydroxynaphtoate, 2-hydroxyethanesulfonate, lactate, maleate, malate, mandelate, methanesulfonate, muconate, 2-naphtalenesulfonate, propionate, succinate, dibenzoyl-L-tartarate, tartrate, p-toluenesulfonate, trimethylacetate, and trifluoroacetate acid and the like, preferably chloride, bromide, phosphate, acetate, fumarate, glucoheptonate, gluconate, glutamate, glycolate, hydroxynaphtoate, lactate, maleate, malate, muconate, propionate, succinate and tartrate, even more preferably chloride or bromide.

As used herein, a pharmaceutically acceptable base may be organic or inorganic. Examples of organic bases comprise diethanolamine, ethanolamine, N-methylglucamine, triethanolamine, tromethamine and the like. Examples of inorganic bases comprise aluminium hydroxide, calcium hydroxide, potassium hydroxide, sodium carbonate and sodium hydroxide.

The contact angle of a substrate is measured according to methods well known to those skilled in the art. For example, one can use a method measuring the contact angle from a drop of water deposited on the surface of a substrate before and after grafting, via a camera, thus enabling to quantify the changes of the hydrophilic or hydrophobic character of the surface of the substrate.

DETAILED DESCRIPTION

I. Method for Grafting a Polymeric Substrate

The present invention relates to a method for grafting a properties-imparting compound onto a polymeric substrate containing carbon-hydrogen (C—H) bonds, preferably an implantable polymeric substrate containing carbon-hydrogen (C—H) bonds, said method comprising:
  a) providing a substrate;
  b) coating the substrate with a properties-imparting compound comprising a photoactive aryl-azide moiety of formula (I):

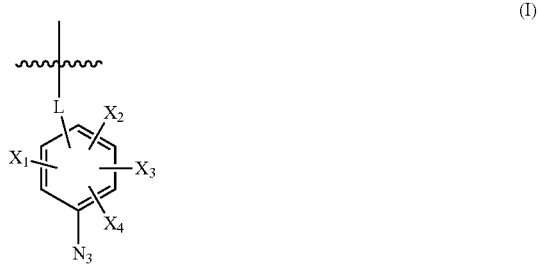

with $X_1$, $X_2$, $X_3$ and $X_4$ independently representing a hydrogen or a fluorine atom, a $C_1$-$C_6$ alkyl group, $NO_2$ or OH and L representing NH, —C(O)O—, —S—, —C(O)NH—, —NHC(O)—, —OC(O)—, —NHC(O)NH—, —NHC(S)

NH—, —C(O)NRC(O)— with R representing a $C_1$-$C_6$alkyl or triazolyl, preferably NH, —C(O)O—, —S—, —C(O)NH—, —NHC(O)—, —OC(O)—, —NHC(O)NH—, or —NHC(S)NH—, even more preferably —C(O)NH—, —NHC(O)—, —C(O)O—, NH or —NHC(S)NH—,
so as to obtain a homogeneous dry layer of said properties-imparting compound coated on at least part of the substrate, and to bring said aryl-azide moiety of formula (VI) into covalent bonding proximity with the carbon-hydrogen bonds of the substrate;
- c) irradiating the coated substrate with a reactive light source, preferably a UV or an IR source, for a time $t_1$ sufficient to form nitrenes that undergo insertion reactions into carbon-hydrogen bonds of the substrate, $t_1$ being equal to or less than 30 minutes;
- d) optionally washing the obtained grafted polymeric substrate;
- e) repeating steps b), c) and optionally d) at least once, advantagesouly at least twice, and preferably at most 9 times, even more preferably steps b), c) and optionally d) are repeated 4 times; and
- f) optionally drying the grafted substrate obtained at the end of step e).

Preferably, L is in para position from the azide group ($N_3$). Therefore, preferably the photoactive aryl-azide moiety is of formula (I'):

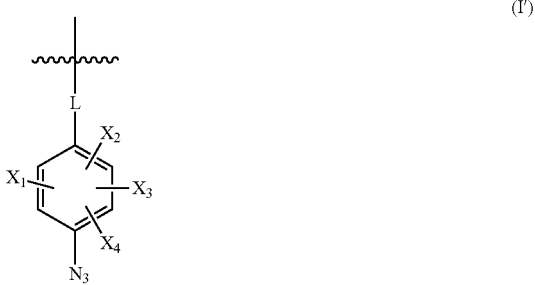

With L and $X_1$ to $X_4$ as defined above and below.

In one embodiment, one of $X_1$ to $X_4$ is OH or $NO_2$, and the others are independently selected from H and $C_1$-$C_6$ alkyl group. Preferably, in this embodiment, one of $X_1$ to $X_4$ is OH or $NO_2$, and the others are H.

In another embodiment, $X_1$ to $X_4$ are a halogen atom. Preferably, in this embodiment, $X_1$ to $X_4$ are a fluorine atom.

In another embodiment, $X_1$ to $X_4$ are H. Advantageously, in this embodiment, L is advantageously NH, —C(O)O—, —S—, —C(O)NH—, —NHC(O)—, —OC(O)—, —NHC(O)NH—, or —NHC(S)NH—, preferably —C(O)NH—, —NHC(O)—, —C(O)O—, NH or —NHC(S)NH—.

Advantageously, the method of the invention does not include any surface modification of the substrate prior to step a). In particular, the method of the invention preferably does not include oxidation, such as chemical or plasma oxidation.

The process of the invention may further contain a step f1) of washing the obtained grafted polymeric substrate, which is preferably carried out between steps e) and f).

The process may also contain a further final step g) of sterilizing the obtained surface-modified substrate, for instance through heating at high temperature.

In a particular embodiment, the method of the invention consists of steps a), b), c), optional step d), e) and optionally f1), f) and g).

I.1. Polymeric Substrate

Typically, the polymeric substrate is selected from aliphatic polyesters and copolyesters, copolymers of aliphatic polyesters and polyethers, polycarbonate, polydioxanone, polypropylene, polyethylene, polyethylene terephthalate, polyethylene oxide, polyurea, poloxamer, poloxamine, silicone, polycarboxylate and polyether ether ketone.

The polymeric substrate may also be selected from ABS (Acrylonitrile butadiene styrene), polystyerene, polyvinylchloride, and polyacrylates.

The substrate may be implantable or non-implantable. Indeed, the feasibility of the method of the invention is not limited to implantable substrates: as indicated above, the only property that is necessary for the method to be applicable to a specific substrate is that it contains C—H bonds, available for the clip chemistry functionalization.

In a particular embodiment, the polymeric substrate is implantable and is selected from aliphatic polyesters and copolyesters, copolymers of aliphatic polyesters and polyethers, polycarbonate, polydioxanone, polypropylene, polyethylene, polyethylene terephthalate, polyethylene oxide, polyurea, poloxamer, poloxamine, silicone, polycarboxylate and polyether ether ketone.

Preferred aliphatic polyesters and copolyesters and copolymers of aliphatic polyesters and polyethers are poly(lactic acid) (PLA), poly(lactic acid-co-glycolic acid) (PLGA), PLA-poloxamer-PLA and polycaprolactone.

The present invention encompasses in particular PLGA in all proportions, i.e. the ratio lactic acid:glycolic acid in the PLGA of the invention is of between 0 and 100, preferably between 50:50 and 85:15, for instance 50:50, 70:30, 75:25, 82:18 and 85:15.

In the PLA polymers, the lactic acid may be either (L)-lactic acid or (D)-lactic acid. The present invention encompasses PLA polymers in any proportions, i.e. the ratio (L)-lactic acid:(D)-lactic acid may be of between 0 and 100, preferably between 50:50 and 98:2 or between 2:98 and 50:50. In particular, the PLA of the invention may be PLA94, PLA100, PLA98, PLA96, PLA70 et PLA50.

The polymeric substrate of the invention may in particular be chosen from Resomer® polymers (marketed by Evonik). In this case, it is advantageously implantable.

The preferred polycaprolactone is poly(ε-caprolactone).

The preferred polycarboxylate of the invention is poly (trimethylene carbonate).

Examples of poloxamers are poloxamers marketed as Pluronic®.

Examples of poloxamines are poloxamines marketed as Tetronic® or polymers disclosed by Leroy et al (see for instance Leroy A., Materials Science and Engineering C (2013), 33(7), 4133-4139; Leroy, A. Biomaterials Science: 3, 4, 617-626 (2015); Morille, Marie) or by Morille et al (see Tran Van-Thanh; Garric, Xavier; et al. Journal Of Controlled Release 170, 1, 99-110, (2013)). An example of polycarbonate is poly(trimethylene carbonate).

In an advantageous embodiment, the substrate is implantable.

In a particular embodiment, the polymeric (implantable) substrate is not degradable. In this embodiment, the polymeric (implantable) substrate is preferably polypropylene, polyethylene, polyethylene terephthalate, polyurea, silicone and polyether ether ketone.

In another particular embodiment, the polymeric substrate is degradable. In this embodiment, the substrate is advantagesouly implantable, and is preferably aliphatic polyesters and copolyesters, copolymers of aliphatic polyesters and polyethers, such as poly(lactic acid) (PLA), poly(lactic acid-co-glycolic acid) (PLGA), PLA-poloxamer-PLA and polycaprolactone (in particular poly(ε-caprolactone)), which are each preferably as described above. Examples of such degradable polymers are in particular described by Nottelet et al (see in particular Journal of Polymer Science 2010, 48, 5891-5898; Mater. Sci. Eng. C 2013, 33(7), 4133-4139; Biomacrocmolcules 2012, 13, 1544-1553; Acta Biomaterialia 2013, 9, 7709-7718).

I.2. Coating

In step b) of the method of the invention, the substrate is coated with the properties-imparting compound so as to obtain a homogeneous dry layer of said properties-imparting compound coated on at least part of the polymeric substrate, and to bring said aryl-azide moiety of formula (I) into covalent bonding proximity with the carbon-hydrogen bonds of the polymeric substrate. To achieve homogeneous coating, various coating techniques may be used. In particular, dip-coating, spray-coating or spin-coating, preferably spray-coating may be used.

Where appropriate, to obtain a dry layer of properties-imparting compound, the coated substrate is then dried, notably under conditions which will preserve the homogeneity of the coating. A drying step is advantageously used when the coating is performed by dip-coating.

Advantageously, the layer is made of polymer with a thickness of between 1 and 50 nm, more preferably between 1 and 20 nm.

The one of skill in the art will adapt the operating conditions of the coating and optionally the drying step so as to obtain the desired homogeneous dry layer, of the desired thickness.

In a particular embodiment, the properties-imparting compound is coated on all the surface of the (implantable) substrate. This embodiment is preferred when the properties-imparting compound is an antifouling or an antibacterial agent.

In another particular embodiment, the properties-imparting compound is coated on part of the surface of the (implantable) substrate. This embodiment is preferred when the properties-imparting compound is useful for medical imaging.

I.3. Reactive Light Source

In the present invention, the reactive light source is preferably a UV source.

Preferably, the reactive light source has a power of between 1 and 400 W, preferably between 4 and 20 W, for instance 8 W.

When the reactive light source is a UV source, its wavelength is preferably of between 10 nm and 380 nm, preferably between 200 nm and 380 nm. For instance, the UV light source has a wavelength of 365 nm or 254 nm, preferably 254 nm.

The reactive light source, in particular when it is a UV light source, is preferably positioned at a distance of 1 to 50 cm, for instance at a distance of between 2 and 5 cm, from the surface (of the substrate) to be irradiated. The one of skill in the art will choose the suitable distance in particular in view of the power of the reactive light source.

Preferably, the reactive light source is a UV source.

I.4. Time of Irradiation $t_1$

As explained above, the Inventors have observed that increasing the time of irradiation increases the degradation of the aryl-azide containing properties-imparting compound, but does not improve the grafting rate.

Therefore, in step b), the coated substrate is irradiated for a time $t_1$ equal to or less than 30 minutes, preferably less than 25 minutes, more preferably less than or 20 minutes.

In addition, $t_1$ should be sufficient to allow formation of nitrenes. In particular, $t_1$ is of at least 30 seconds, preferably at least 1 minute.

Most preferably, $t_1$ is of 1, 5 or 20 minutes.

I.5. Washing Step d)

Washing step d) is preferably carried out by ultrasonication (for instance by immersion in an ultrasonic bath) and/or by rinsing with a solvent, preferably an aqueous solvent or an alcohol such as methanol. In a particular embodiment, the washing is carried out by ultrasonication by immersion in an ultrasonic aqueous bath at room temperature and/or by rinsing with water or methanol.

I.6. Repeating (Step e)

The number of repetition may be easily determined by the one of skill in the art, in particular in view of the contact angle or by the grafting rate of the obtained grafted substrate.

The Inventors have observed that the number of repetitions depends on the "compatibility" of the polymeric substrate with the properties-imparting compound. A hydrophilic substrate is generally more compatible with a hydrophilic properties-imparting compound, while it is less compatible with a hydrophobic properties-imparting compound, and vice versa.

The Inventors have thus observed that the less the substrate and the properties-imparting compound are "compatible", the higher the number of repetitions should be.

However, it was also observed that optimal results are generally obtained with 4 repetitions.

I.7. Properties-Imparting Compound

The properties imparting compound of the method of the invention contains an aryl-azide moiety of formula (I) above.

Typically, the properties-imparting compound provides anti-fouling properties, antibacterial properties, or renders the substrate radio-opaque or visible in medical imaging, such as MRI, fluorescence imaging, or near infrared imaging.

The properties-imparting may be a polymer or a small molecule.

In a particular embodiment, the properties-imparting compound is a polymer. In this embodiment, the polymer is a copolymer comprising repeated units A, said repeated units A comprising the aryl-azide moiety of formula (I) as defined above.

The copolymer may comprise only one or two repeated units A at the end of the polymeric chain. In this case, the copolymer is referred to as a "chain-end polymer". An example of chain-end polymer is obtained when the copolymer is a polysarcosine or polylactone copolymer. For instance, in this case, in the repeated unit A comprising the aryl-azide moiety of formula (I) L is NH. The corresponding free amine acts as an initiator of the reaction with a lactone monomer or a cyclic anhydride.

Alternatively, the copolymer is a block- or gradient-copolymer with a block or a region rich in repeated units A, said repeated units A comprising the aryl-azide moiety of formula (I) as defined above.

In this embodiment, the block- or gradient-copolymer contains at least repeated units A and B, wherein:
repeated units A comprises the aryl-azide moiety of formula (I) as defined above, and
repeated units B lacks the aryl-azide moiety of formula (I) as defined above.

It is understood that repeated units A and B are compatible, i.e. they preferably derive from monomers containing polymerisable group which are able to polymerize under the same reaction conditions. Advantageously, the repeated units A and B derive from monomers containing the same polymerisable group.

For instance, when B is derived from a vinylic monomer, A is preferably derived from a vinylic monomer comprising the aryl-amino moiety of formula (I) as defined above. In a similar way, when B is derived from an oxazoline monomer, A is preferably derived from a oxazoline monomer comprising the aryl-amino moiety of formula (I) as defined above. When B is derived from an sarcosine monomer, A is preferably derived from a sarcosine monomer comprising the aryl-amino moiety of formula (I) as defined above. When B is derived from a (meth)acrylate monomer, A is preferably derived from a (meth)acrylate monomer comprising the aryl-amino moiety of formula (I) as defined above.

In particular, monomer A may be of formula A1:

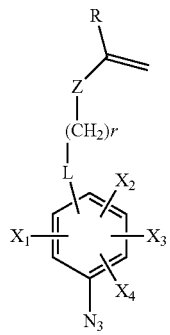

(A1)

with $X_1$ to $X_4$ and L as defined above
Z representing a bond or —O(O)C—,
r an integer of between 0 and 10, preferably 0 or 2, and
R selected from H, a $C_1$-$C_6$ alkyl or an aryl group.
Preferably, X is H, r is 0 or 2 and R is selected from H or $CH_3$.
Advantageously, L is —C(O)O— or —O(O)C—. Preferably L —O(O)C— and Z is a bond.
In another particular embodiment, monomer A may be of formula A2:

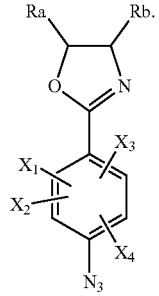

(A2)

with $X_1$ to $X_4$ as defined above
Ra and Rb each independently selected from H, a $C_1$-$C_6$ alkyl or an aryl group.
Preferably, X is H, and Ra and Rb are H.
In a particular embodiment, a first homopolymer or block-copolymer comprising a reactive end-group serves as a polymerization initiator for forming the next block of the final block copolymer. For instance, a first polyoxazoline block-copolymer or homopolymer (for instance a homopolymer obtained by polymerizing the monomers of formula A2 above) may serve as an initiator for the polymerization of monomers of formula B1 below, thus leading to a polyoxazoline-polysarcosine block copolymer:

(B1)

with R representing H or a $C_1$-$C_6$ alkyl group, preferably a $C_1$-$C_6$ alkyl group
as an initiator for forming a PEG block, thus leading to a polyoxazoline-PEG block copolymer.

Advantageously, the molar ratio of repeated units A on repeated units B (repeated units A/repeated units B) is of between 0.01% and 50%, preferably of between 0.1% and 20%, even more preferably between 0.5% and 10%.

I.7.a Antifouling and Antibacterial Agents as Properties-Imparting Compound

In a particular embodiment, the properties-imparting compound provides anti-fouling or antibacterial properties.

In this embodiment, the substrate may be implantable or non-implantable.

Suitable anti-fouling or antibacterial polymers are for instance described by Timofeeva et al (Appl. Microbiol. Biotechnol. 2011, 89, 475-492), Campoccia et al (Biomaterials 2013, 34, 8533-8554), and Kenawy et al (Biomacromolecules, 2007, 8(5), 1359-1384).

In the case where the properties-imparting compound is an antifouling agent, it may be a hydrophilic block- or gradient-copolymer with a block or a region rich in repeated units A, said repeated units A comprising the photoactive aryl-azide moiety of formula (I) as defined above with the nitrogen atom covalently bound to the surface of the surface-modified substrate.

In the case where the properties-imparting compound is an antibacterial agent, it may be a cationic block- or gradient-copolymer with a block or a region rich in repeated units A, said repeated units A comprising the photoactive aryl-azide moiety of formula (I) as defined above with the nitrogen atom covalently bound to the surface of the surface-modified substrate.

In particular, the hydrophilic or cationic block- or gradient-copolymer contains at least repeated units A and B, wherein repeated units A comprise the photoactive aryl-azide moiety of formula (I) as defined above, and repeated units B lack the photoactive aryl-azide moiety of formula (I) as defined above. Preferably, the molar ratio of repeated units A on repeated units B (repeated units A/repeated units B) is of between 0.01% and 50%, preferably of between 0.1% and 20%, even more preferably between 0.5% and 10%.

Typically, the hydrophilic or cationic block- or gradient-copolymer including repeated units A comprising the photoactive aryl-azide moiety of formula (I) as defined above, is:
 a poly(ethylene glycol),
 a poly(ethylene oxide),
 a poly((meth)acrylatePEG),
 poly(($C_1$-$C_6$)alkylamino(meth)acrylate),
 a linear poly(quaternary ammonium) with a molecular weight of less than 20 000 g·mol$^{-1}$, in particular between 1000 g/mol$^{-1}$ and 20 000 g·mol$^{-1}$, in particular quaternized poly(N—(C$_1$-C$_6$)alkyl)(meth)acrylamide) or quaternized poly(N-(hydroxyl(C$_1$-C$_6$)alkyl)(meth)acrylamide, in particular quaternized (polydimethylamino ethylmethacryclate), wherein the quaternized polymers are quaternized with a C$_1$-C$_{15}$ alkyl, preferably a C$_3$-C$_{10}$ alkyl, more preferably a C$_7$-C$_9$ alkyl, a zwitterionic poly(betaine), i.e. an ampholytic polymer in which pendant groups have a betaine-type structure such as phosphonate-betaine, sulfonate-betaine or carboxylate-betaine), a poly(vinylpyrrolidone), a polylysine, a polyoxazoline, such as poly(-(C$_1$-C$_6$)alkyl)oxazoline), in particular poly(methyloxazoline) and poly(ethyloxazoline), a polysarcosine block- or gradient-copolymer, or a polyoxazoline-polysarcosine block copolymer.

Also considered are polyoxazines and polyoxazoline-polyoxazine copolymers.

Preferably, the hydrophilic (preferably block- or gradient-) copolymer is a poly((C$_1$-C$_6$)alkylamino(meth)acrylate), a polyoxazoline (in particular poly(methyloxazoline) and poly(ethyloxazoline)) or a polysarcosine block- or gradient-copolymer.

For instance, the hydrophilic (preferably block- or gradient-) copolymer is a poly((C$_1$-C$_6$)alkylamino(meth)acrylate) obtained by polymerization of monomers of formula A1, as defined above, with monomers of formula (B2):

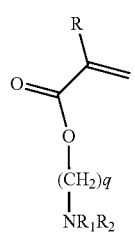

(B2)

with q an integer of between 1 and 10, preferably between 2 and 6, more preferably 2, R being H or a C$_1$-C$_6$alkyl, preferably H or CH$_3$, and R$_1$ and R$_2$ each independently selected from H and a C$_1$-C$_6$ alkyl.

For instance, R is H or CH$_3$, q is 2 and R$_1$ and R$_2$ are both CH$_3$.

The hydrophilic (preferably block- or gradient-) copolymer may also be a polyoxazoline obtained by polymerizing monomers of formula A2 as defined above with monomers of formula B3:

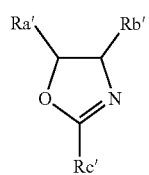

(B3)

with Ra', Rb' and Rc' each independently selected from H, a C$_1$-C$_6$ alkyl or an aryl group. Preferably Rc' is a C$_1$-C$_6$ alkyl or an aryl group and Ra' and Rb' are each independently selected from H and a C$_1$-C$_6$ alkyl. For instance, Ra' and Rb' are H and Rc' is a methyl.

In a particular embodiment, the properties-imparting compound is an antibacterial agent covalently bound to the surface of the substrate through a nitrogen atom.

In a first embodiment, the antibacterial agent is a copolymer (preferably a cationic copolymer) selected from: a quaternized poly(vinylpyridine), a quaternized poly(dimethylaminoethylacrylate), a linear quaternized poly(ethyleneimine), a polylysine, a quaternized polylysine, a copolyester of quaternized poly(5-Amino-δ-valerolactone), wherein the quaternized polymers are quaternized with a C$_1$-C$_{15}$ alkyl, preferably a C$_3$-C$_{10}$ alkyl, more preferably a C$_7$-C$_9$ alkyl. Also contemplated are quaternized forms of partially hydrolyzed polyoxazoline such as quaternized polyoxazoline-polyethyleneimine copolymers, wherein the quaternized polymers are quaternized with a C$_1$-C$_{15}$ alkyl, preferably a C$_3$-C$_{10}$ alkyl, more preferably a C$_7$-C$_9$ alkyl.

The copolyester of quaternized poly(5-Amino-δ-valerolactone) may in particular be as described in Blanquer et al. J Pol Sci Part A Pol Chem (2010), 48(24), 5891-5898 and Nottelet et al. Biomacromolecules (2012), 13, 1544-1553.

In a second embodiment, the antibacterial agent is a quaternary ammonium of formula (IIa):

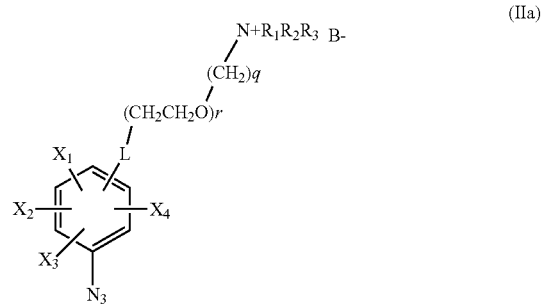

(IIa)

with X$_1$ to X$_4$ and L as defined above, q an integer from between 0 and 10, preferably between 1 and 8, r an integer from between 0 and 3000, preferably between 0 and 500, and R$^1$ and R$^2$ each independently selected from a hydrogen atom or a C$_1$-C$_6$ alkyl group, R$^3$ independently selected from a hydrogen atom or a C$_1$-C$_9$ alkyl group and B— representing a pharmaceutically acceptable anion.

For instance, L is NH, X is H, r is 0, q is 3, R$^1$, R$^2$ and R$^3$ are each methyl and B— is bromine.

In a third embodiment, the antibacterial agent is a quaternary phosphonium of formula (IIb):

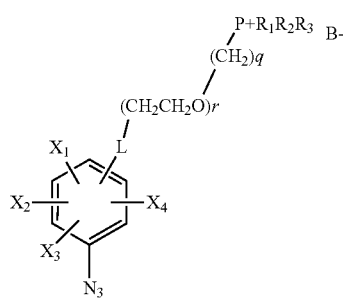

(IIb)

with $X_1$ to $X_4$ and L as defined above,
q an integer from between 0 and 10, preferably between 1 and 8,
r an integer from between 0 and 3000, preferably between 0 and 500,
$R^1$, $R^2$ each independently selected from a hydrogen atom or a $C_1$-$C_6$ alkyl group, $R^3$ independently selected from a hydrogen atom or a $C_1$-$C_9$ alkyl group, and B— representing a pharmaceutically acceptable anion.

In a fourth embodiment, the antibacterial agent is a quaternary pyridinium of formula (IIc)

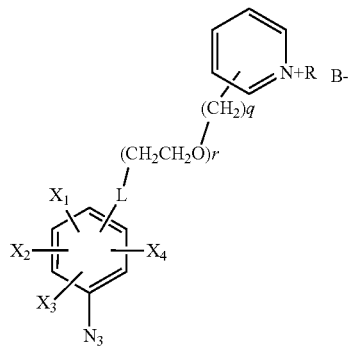

(IIc)

with $X_1$ to $X_4$ and L as defined above,
q an integer from between 0 and 10, preferably between 1 and 8,
r an integer from between 0 and 3000, preferably between 0 and 500,
R selected from a hydrogen atom or a $C_1$-$C_9$ alkyl group, and B— representing a pharmaceutically acceptable anion.

In a fifth embodiment, the antibacterial agent is an antibacterial peptide of 25 amino acids or less (preferably 20 amino-acids or less) and preferably selected from a polyarginine (such as octaarginine Arg8), aurein and polymyxin B, and comprising a pending group of formula (I) as defined above.

Preferably, in this fifth embodiment, the antibacterial agent is selected from a polyarginine (such as octaarginine Arg8) comprising one pending photoactive aryl-azide moiety of formula (I) as defined above.

I.7.b. Properties-Imparting Compound Useful for Medical Imaging

In a particular embodiment, the properties-imparting compound is useful in medical imaging. In particular, the properties-imparting compound is a radio-opaque iodinated contrast agent, a complex of a lanthanide (in particular with a linear or macrocyclic polyamine), or a fluorescent compound, including a near-infrared fluorescent compound.

In this embodiment, the substrate is preferably implantable.

Radio-Opaque Compounds

In a particular embodiment, the properties-imparting compound is radiopaque.

In a particular embodiment, the radio-opaque compound may be an iodinated compound of formula (III):

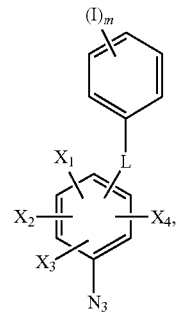

(III)

with $X_1$ to $X_4$ and L as defined above, and m representing 1, 2, 3 or 4.

More specifically, the radio-opaque compound may be an iodobenzyl derivative of formula (IIIa):

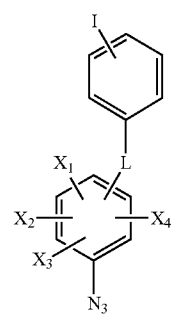

(IIIa)

with $X_1$ to $X_4$ and L as defined above,
or a triiodobenzyl of formula (IIIb):

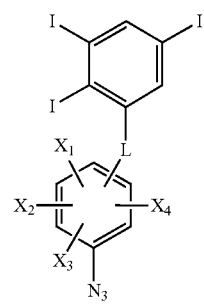

(IIIb)

with $X_1$ to $X_4$ and L as defined above.
Preferably, $X_1$ to $X_4$ represent H.
For instance, the radio-opaque compound is a triiodobenzyl of formula (IIIb) with $X_1$ to $X_4$ representing H and L representing —NHC(O)— or —C(O)NH—.

In another particular embodiment, the radio-opaque compound is a polymer comprising an iodinated moiety of formula

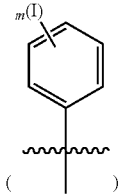

with m representing 1, 2, 3 or 4, such as an iodophenyl moiety

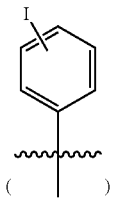

or a triiodophenyl moiety

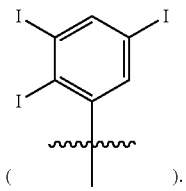 [SMILES: *c1cc(I)cc(I)c1I]

For instance, the polymer is a block or gradient copolymer of monomers of formula A1 as defined above and of monomers of formula B4, such as B4a or B4b:

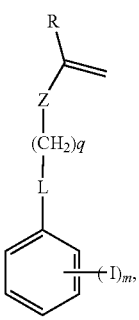
(B4)

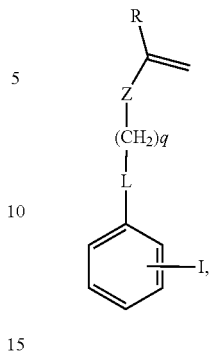
(B4a)

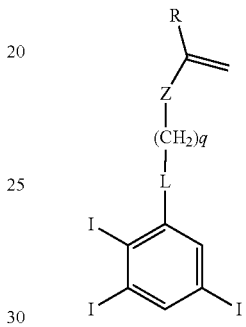
(B4b)

with L as defined above, in particular representing —C(O)O— or —O(O)C—, m representing 1, 2, 3 or 4

Z representing a bond or —OC(O)— q an integer from between 0 and 10, preferably between 1 and 8, more preferably 2, and and with R representing H or a $C_1$-$C_6$ alkyl group, preferably H or $CH_3$.

Preferably, at least one of L and Z represents —OC(O)— so that monomers (B3a) and (B3b) are (meth)acrylate monomers.

Advantageously, L represents —C(O)O— and Z represents —OC(O)—.

Preferably, L represents —C(O)O—, q is 2 R is H or $CH_3$, and Z represents —OC(O)—.

PCL copolymers similar to those described by Nottelet et al (RSC Advances 2015, 5, 84125-84133) are also contemplated in the present invention.

MRI

In a particular embodiment, the properties-imparting compound acts as a MRI contrast agent.

Typically, the properties-imparting compound comprises a gadolinium complex of DOTA (1,4,7,10-tetraazacyclododecan-1,4,7,10-tetraacetic acid), DTPA (diethylenetriaminopentaacetic acid), DO3A (1,4,7,10-tetraazacyclododecan-1,4,7-triacetic acid), HPDO3A (10-(2-hydroxypropyl)-1,4,7,10-tetraazacyclododecan-1,4,7-triacetic acid), TRITA (1,4,7,10-Tetrakis(carboxymethyl)-1,4,7,10-tetraazacyclotridecane), TETA (1,4,8,11-Tetrakis(carboxymethyl)-1,4,8,11-Tetraazacyclotetradecane), BOPTA (4-carboxy-5,8,11-tris(carboxymethyl)-1-phenyl-2-oxa-5,8,11-triazatridecan-13-oic acid), NOTA (1,4,7-triazacyclononane-N,N',N44-triacetic acid), PCTA (3,6,9,15-tetraazabicyclo[9.3.1]pentadeca-1(15),11,13-triene-3,6,9- triacetic acid), DOTMA ((alpha, alpha', alpha'', alpha''')-tetramethyl-1,4,7,10-tetraazacyclododecan-1,4,7,10-tetraacetic acid), AAZTA (6-amino-6-methylperhydro-1,4-diazepinetetraacetic acid) and HOPO (1-hydroxypyridin-2-one), preferably DTPA, DOTA, NOTA, DO3A and PCTA, even more preferably DTPA or DOTA.

It may in particular be of formula (IV):

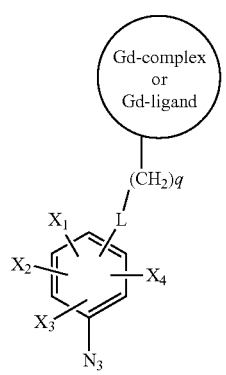

(IV)

with $X_1$ to $X_4$ and L as defined above, q an integer from between 0 and 10, preferably between 1 and 8, more preferably 2, and Gd-complex a gadolinium ligand in particular as listed above, preferably DTPA, DOTA, NOTA, DO3A and PCTA, even more preferably DTPA or DOTA, as the free base or colmplexed with gadolinium.

In a particular embodiment, the properties-imparting compound is of formula (IVa) or (IVb):

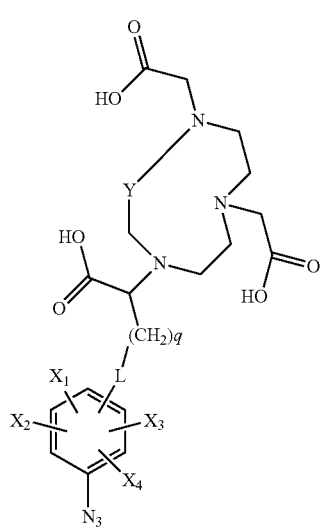

(IVa)

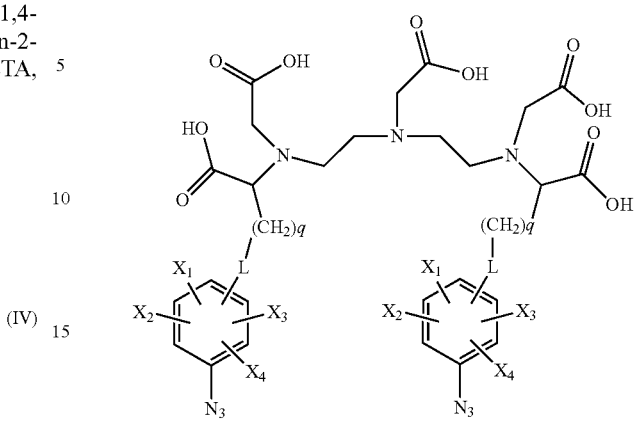

(IVb)

with $X_1$ to $X_4$ and L as defined above,
q an integer from between 1 and 10, preferably between 2 and 8, more preferably 2, and Y selected from a bond, a —$CH_2N(CH_2CH_2COOH)CH_2CH_2$— group, or a

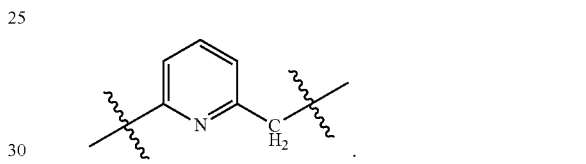

In formulae (IV) and (IVa), preferably, X is H and L is a —NHC(O)— or a —C(O)NH— group.

The compounds of formulae (IV), (IVa) and (IVb) may be used as the free base or complexed with gadolinium. In the latter case, where appropriate, it is preferably used as a salt with a pharmaceutically acceptable base, such as NaOH or methylglucamine.

The complexation with gadolinium may be carried out either prior to grafting or after grafting of the compound of formulae (IV), (IVa) and (IVb).

It may also be a block or gradient copolymer of monomers A1 as defined above and of monomers B5 of the following formula:

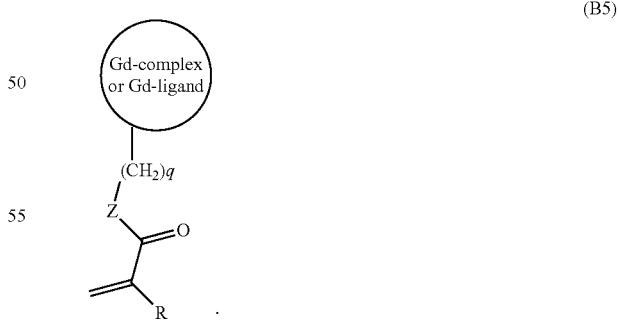

(B5)

with q an integer from between 1 and 10, preferably between 2 and 8, more preferably 2, Z being O or NR', with R' a hydrogen atom or a $C_1$-$C_6$alkyl group (preferably a hydrogen atom), R selected from a hydrogen atom or a $C_1$-$C_6$ alkyl group or an aryl group, and "Gd-complex or ligand" a gadolinium ligand, in particular as listed above, preferably DOTA, NOTA, DO3A and PCTA, even more preferably DOTA, as the free base or complexed with gadolinium. In the latter case, where appropriate, it is preferably used as a salt with a pharmaceutically acceptable base, such as NaOH or methylglucamine.

Preferably R is H or CH$_3$ and q is 2.

For instance, monomer B5 is of formula B5a, B5b or B5c below:

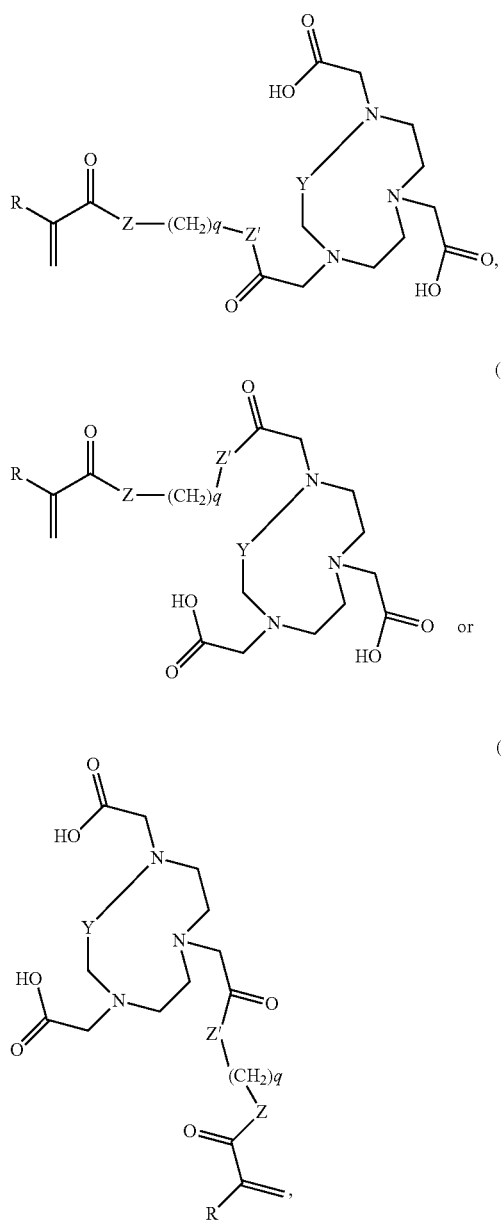

with q an integer from between 1 and 10, preferably between 2 and 8, more preferably 2, Z and Z' being each independently O or NR', with R' a hydrogen atom or a C$_1$-C$_6$alkyl group (preferably a hydrogen atom), R selected from a hydrogen atom or a C$_1$-C$_6$ alkyl group or an aryl group, and Y selected from a bond, a —CH$_2$N(CH$_2$CH$_2$COOH)CH$_2$CH$_2$— group, or a

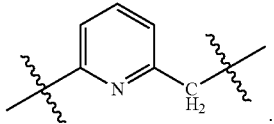 [SMILES: *Cc1cccc(*)n1]

The compound of formula (B4a), (B4b) and (B4c) may be used as the free base or complexed with gadolinium. In the latter case, where appropriate, they are preferably used as a salt with a pharmaceutically acceptable base, such as NaOH or methylglucamine.

Preferably R is H or CH$_3$ and q is 2.

The complexation with gadolinium may be carried out either prior to grafting or after grafting of the compound of formula (B5), (B5a), (B5b) or (B5c).

Alternatively, the properties-imparting compound may comprise a gadolinium complex of a macromolecular ligand such as PCL, poly(meth)acrylate, poly(5-Amino-δ-valerolactone) copolymers, in particular as described in patent applications WO2013084204A1 and WO2011004332.

In this embodiment, the properties-imparting compound may in particular be a copolymer containing a propargyl pending groups such as described for instance in WO 2011/004332 or WO 2013/084204 or in articles by Nottelet et al (see in particular Biomacrocmolecules 2013, 14, 3626-3634; Biomacrocmolecules 2014, 15, 4351-4362; RSC Adv. 2016, 6, 5754-5760), and further including the aryl-azide moiety of formula (I) as defined above.

For instance, such a copolymer is obtained by polymerizing the monomer of formula A1 as defined above and acrylic monomers, such as propargyl(meth)acrylate or a mixture of C$_1$-C$_6$alkyl (meth)acrylate and propargyl(meth)acrylate. The propargyl pending group is then reacted with a gadolinium complex or ligand containing an azide group through a Huysgens reaction, or with a gadolinium complex or ligand containing a thiol group through a thiol-yne reaction to obtain a copolymer visible in MRI.

The complexation with gadolinium may be carried out either prior to grafting or after grafting of the copolymer.

Fluorescence and IR Imaging

In a particular embodiment, the properties-imparting compound is useful as a contrast agent for fluorescence or near IR imaging.

In a first embodiment, the properties-imparting compound is a rhodamine derivative of formula (Va):

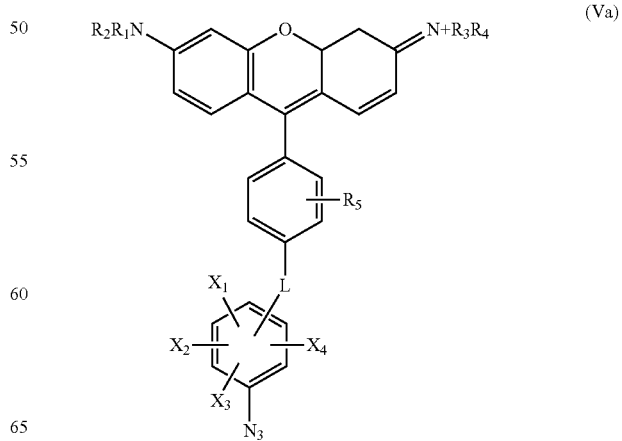

with $X_1$ to $X_4$ and L as defined above, $R^1$, $R^2$, $R^3$ and $R^4$ each independently selected from a hydrogen atom or a $C_1$-$C_6$ alkyl group, and $R^5$ selected from a hydrogen atom, a COOH or a $C(O)OC_1$-$C_6$ alkyl group.

In this first embodiment, preferably L is —NHC(S)NH— and X is H. Advantageously, $R^5$ is COOH. Preferably, $R^1$, $R^2$, $R^3$ and $R^4$ are each ethyl ($CH_2CH_3$).

Typically, in this embodiment, compound (Va) is a salt with $B^-$, wherein $B^-$ is a pharmaceutically acceptable anion, such as a halogen anion, typically $Cl^-$ or $Br^-$, preferably $Cl^-$.

In a second embodiment, the properties-imparting compound is a cyanin derivative of formula (Vb):

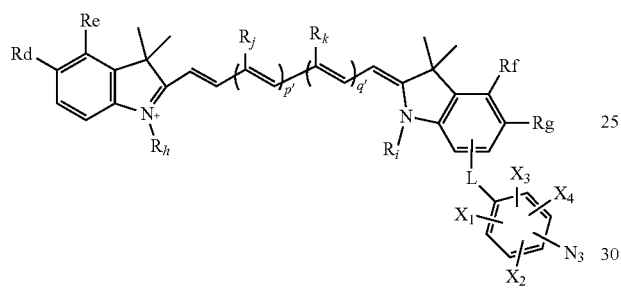

with $X_1$ to $X_4$ and L as defined above, p' being 0 or 1, q' being 0 or 1 if p' is 0 then $R_k$ is H, if q' is 0 then $R_j$ is H, if p' is 1 and q' is 1, then $R_j$ and $R_k$ are both H or taken together, form a —$CH_2CH_2CH_2$— bridging group, $R_d$ is selected from H and $SO_3Na$, and $R_e$ is H or taken together, $R_d$ and $R_e$ form a —$CH_2CH_2CH_2$— or —CHCHCH— bridging group, $R_g$ is selected from H and $SO_3Na$, and $R_f$ is H, or taken together, $R_f$ and $R_g$ form a —$CH_2CH_2CH_2$— or —CHCHCH— bridging group, $R_h$ being selected from a ($C_1$-$C_6$)alkyl group, optionally substituted with a $SO_3$— or a COOH group, preferably on the last carbon atom, $R_i$ being selected from a ($C_1$-$C_6$)alkyl group, optionally substituted with a $SO_3Na$ or a COOH group, preferably on the last carbon atom.

Preferably, in this embodiment, taken together, $R_d$ and $R_e$ form a —CHCHCH— bridging group, and $R_f$ and $R_g$ form —CHCHCH— bridging group. Then, $R_h$ is advantageously a $C_4$-alkyl group substituted with a $SO_3$— group on the last carbon (i.e. a group —$(CH_2)_5$—$SO_3$—), and $R_i$ is advantageously a $C_4$-alkyl group substituted with a $SO_3Na$ group on the last carbon (i.e. a group —$(CH_2)_5$—$SO_3Na$). In this embodiment, $R_j$ and $R_k$ are preferably both H and p' and q' are preferably both 1.

Typically, in this embodiment, compound (Vb) is a salt with $B^-$, wherein $B^-$ is a pharmaceutically acceptable anion, such as a halogen anion, typically $Cl^-$ or $Br^-$, preferably $Cl^-$.

In a third embodiment, the properties-imparting compound is a fluorescein derivative of formula (Vc):

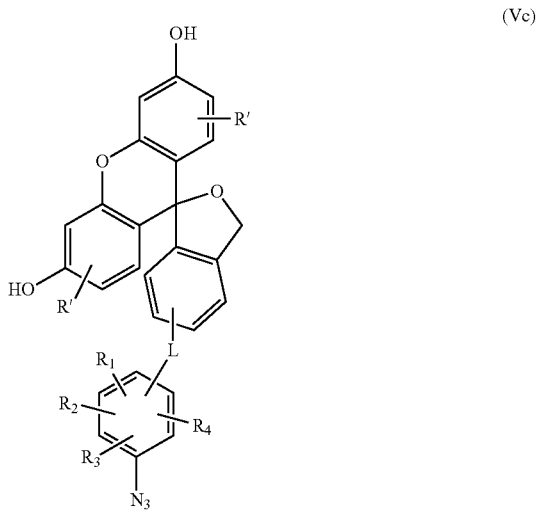

with $X_1$ to $X_4$ and L as defined above, and R' representing H, or a —$CH_2CH_2COOH$ or —CH=CHCOOH group.

Preferably, in this embodiment, L is —NHC(S)NH— and X is H. Advantageously, R' is H.

For fluorescence imaging, the rhodamine derivatives of formula (Va) as defined above are preferably used.

For near IR imaging, the fluoresceine derivative of formula (Vc) or the cyanin derivative of formula (Vb) as defined above are preferably used.

I.8. Miscellaneous

The method of the invention encompasses all combinations of the particular and preferred embodiments described above.

II. Intermediates Containing an Aryl-Azide Moiety of Formula (I)

The present invention further relates to intermediates containing an aryl-azide moiety of formula (I) as defined above.

In particular, the present invention relates to compounds of formula (IIa), (IIb), (IIc), (III), (IIIa), (IIIb), (IV), (IVa), (IVb), (Va), (Vb) and (Vc) as defined above.

In particular, the present invention concerns the compounds of formula (IV), (IVa) and (IVb) either as the free base or as the gadolinium complex.

The present invention further relates to the monomer of formula A2 as defined above.

III. Surface Modified Polymeric Substrate

The present invention relates to a surface-modified polymeric substrate, in particular a polymeric implantable substrate, grafted with a properties-imparting compound through the nitrogen atom of an aryl-amino moiety of formula (VI):

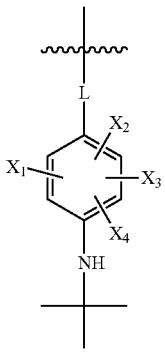

(VI)

with $X_1$, $X_2$, $X_3$ and $X_4$ independently representing a hydrogen or a fluorine atom, a $C_1$-$C_6$ alkyl group, $NO_2$ or OH, and L representing NH, —C(O)O—, —S—, —C(O)NH—, —NHC(O)—, —OC(O)—, —NHC(O)NH—, —C(O)NRC(O)— with R representing a $C_1$-$C_6$alkyl or triazolyl, preferably NH, —C(O)O—, —S—, —C(O)NH—, —NHC(O)—, —OC(O)—, —NHC(O)NH—, or —NHC(S)NH—, even more preferably —C(O)NH—, —NHC(O)—, —C(O)O—, NH or —NHC(S)NH—, said properties-imparting compound providing anti-fouling properties, antibacterial properties, or rendering the substrate radio-opaque or visible in medical imaging, such as MRI fluorescence imaging or visible by near infrared imaging, provided that when said properties-imparting compound is a polymer, it is a block- or gradient-copolymer with a block or a region rich in repeated units A, said repeated units A comprising the aryl-amino moiety of formula (VI) as defined above with the nitrogen atom covalently bound to the surface of the surface-modified substrate.

Preferably, L is in para position from the azide group ($N_3$). Therefore, preferably the photoactive aryl-azide moiety is of formula (I'):

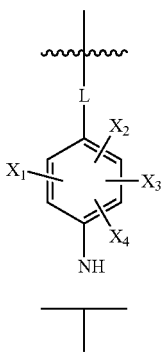

(VI')

With L and $X_1$ to $X_4$ as defined above and below.

In one embodiment, one of $X_1$ to $X_4$ is OH or $NO_2$, and the others are independently selected from H and $C_1$-$C_6$ alkyl group. Preferably, in this embodiment, one of $X_1$ to $X_4$ is OH or $NO_2$, and the others are H.

In another embodiment, $X_1$ to $X_4$ are a halogen atom. Preferably, in this embodiment, $X_1$ to $X_4$ are a fluorine atom.

In another embodiment, $X_1$ to $X_4$ are H. Advantageously, in this embodiment, L is advantageously NH, —C(O)O—, —S—, —C(O)NH—, —NHC(O)—, —OC(O)—, —NHC(O)NH—, or —NHC(S)NH—, preferably —C(O)NH—, —NHC(O)—, —C(O)O—, NH or —NHC(S)NH—.

The surface-modified polymeric substrate of the invention is in particular implantable. In such case, it is typically biocompatible.

III.1 Substrate

Typically, the polymeric (implantable) substrate is defined above in connection with the method of the invention.

III.2. Polymeric Properties-Imparting Compound

The properties-imparting compound of the substrate of the invention contains an aryl-amino moiety of formula (VI) above.

The properties-imparting compound may be a polymer or a small molecule.

In a particular embodiment, the properties-imparting compound is a polymer. In this embodiment, the polymer is a copolymer comprising repeated units C, said repeated units C comprising the aryl-amino moiety of formula (VI) as defined above.

The copolymer is a block- or gradient-copolymer with a block or a region rich in repeated units C, said repeated units C comprising the aryl-amino moiety of formula (VI) as defined above.

In this embodiment, the block- or gradient-copolymer contains at least repeated units C and D, wherein:
repeated units C comprises the aryl-amino moiety of formula (VI) as defined above, and
repeated units D lacks the aryl-amino moiety of formula (VI) as defined above.

It is understood that repeated units C and D are compatible, i.e. they preferably derive from monomers containing polymerisable group which are able to polymerize under the same reaction conditions. Advantageously, the repeated units C and D derive from monomers containing the same polymerisable group.

For instance, when D is derived from a vinylic monomer, C is preferably derived from a vinylic monomer comprising the aryl-amino moiety of formula (I) as defined above. In a similar way, when D is derived from an oxazoline monomer, C is preferably derived from a oxazoline monomer comprising the aryl-amino moiety of formula (I) as defined above. When D is derived from an sarcosine monomer, C is preferably derived from a sarcosine monomer comprising the aryl-amino moiety of formula (I) as defined above. When D is derived from a (meth)acrylate monomer, C is preferably derived from a (meth)acrylate monomer comprising the aryl-amino moiety of formula (I) as defined above.

In particular, monomer C may be derived from a monomer of formula A1 as defined above.

In another particular embodiment, monomer C may be of formula A2 as defined above. Advantageously, the molar ratio of repeated units C over repeated units D (repeated units C/repeated units D) is of between 0.01% and 50%, preferably of between 0.1% and 20%, even more preferably between 0.5% and 10%.

III.2.a Antifouling and Antibacterial Agents as Properties-Imparting Compound

In a particular embodiment, the properties-imparting compound provides anti-fouling or antibacterial properties.

In the case where the properties-imparting compound is an antifouling agent, it may be a hydrophilic block- or gradient-copolymer with a block or a region rich in repeated units C, said repeated units C comprising the photoactive aryl-amino moiety of formula (VI) as defined above with the nitrogen atom covalently bound to the surface of the surface-modified substrate.

In the case where the properties-imparting compound is an antibacterial agent, it may be a cationic block- or gradient-copolymer with a block or a region rich in repeated units C, said repeated units C comprising the photoactive aryl-amino moiety of formula (VI) as defined above with the nitrogen atom covalently bound to the surface of the surface-modified substrate.

In particular, the hydrophilic or cationic block- or gradient-copolymer contains at least repeated units C and D, wherein repeated units C comprise the aryl-amino moiety of formula (VI) as defined above, and repeated units D lack the aryl-amino moiety of formula (VI) as defined above. Preferably, the molar ratio of repeated units C over repeated units D (repeated units C/repeated units D) is of between 0.01% and 50%, preferably of between 0.1% and 20%, even more preferably between 0.5% and 10%.

Typically, the hydrophilic or cationic block- or gradient-copolymer including repeated units C comprising the aryl-amino moiety of formula (VI) as defined above, is:

a poly(ethylene glycol), a poly(ethylene oxide), a poly((meth)acrylatePEG), poly(($C_1$-$C_6$)alkylamino(meth)acrylate), a linear poly(quaternary ammonium) such as, with a molecular weight of less than 20 000 g·mol$^{-1}$, in particular between 1000 g/mol$^{-1}$ and 20 000 g·mol$^{-1}$, in particular quaternized poly(N—($C_1$-$C_6$)alkyl)(meth)acrylamide) or quaternized poly(N-(hydroxyl($C_1$-$C_6$)alkyl)(meth)acrylamide, in particular quaternized (polydimethylamino ethylmethacrylate), wherein the quaternized polymers are quaternized with a $C_1$-$C_{15}$ alkyl, preferably a $C_3$-$C_{10}$ alkyl, more preferably a $C_7$-$C_9$ alkyl a zwitterionic poly(betaine), i.e. an ampholytic polymer in which pendant groups have a betaine-type structure such as phosphonate-betaine, sulfonate-betaine or carboxylate-betaine), a poly(vinylpyrrolidone), a polylysine, a polyoxazoline, such as poly(-($C_1$-$C_6$)alkyl)oxazoline), in particular poly(methyloxazoline) and poly(ethyloxazoline), a polysarcosine block- or gradient-copolymer, or a polyoxazoline-polysarcosine block copolymer.

Also considered are polyoxazines and polyoxazoline-polyoxazine copolymers.

Preferably, the hydrophilic block- or gradient-copolymer is a poly(($C_1$-$C_6$)alkylamino(meth)acrylate), a polyoxazoline (in particular poly(methyloxazoline) and poly(ethyloxazoline)) or a polysarcosine block- or gradient-copolymer.

For instance, the hydrophilic block- or gradient-copolymer is a poly(($C_1$-$C_6$)alkylamino(meth)acrylate) obtained by cationic polymerization of monomers of formula A1, as defined above, with monomers of formula (B1) as defined above.

The hydrophilic block- or gradient-copolymer may also be a polyoxazoline obtained by polymerizing monomers of formula A2 as defined above with monomers of formula B2 as defined above.

In a particular embodiment, the properties-imparting compound is an antibacterial agent covalently bound to the surface of the substrate through a nitrogen atom.

In a first embodiment, the antibacterial agent is a copolymer (preferably a cationic copolymer) selected from: a quaternized poly(vinylpyridine), a quaternized poly(dimethylaminoethylacrylate), a linear quaternized poly(ethyleneimine), a polylysine, a quaternized polylysine, a copolyester of quaternized poly(5-Amino-δ-valerolactone), wherein the quaternized polymers are quaternized with a $C_1$-$C_{15}$ alkyl, preferably a $C_3$-$C_{10}$ alkyl, more preferably a $C_7$-$C_9$ alkyl. Also contemplated are quaternized forms of partially hydrolyzed polyoxazoline such as quaternized polyoxazoline-polyethyleneimine copolymers, wherein the quaternized polymers are quaternized with a $C_1$-$C_{15}$ alkyl, preferably a $C_3$-$C_{10}$ alkyl, more preferably a $C_7$-$C_9$ alkyl.

The copolyester of quaternized poly(5-Amino-δ-valerolactone) may in particular be as described in Blanquer et al. J Pol Sci Part A Pol Chem (2010), 48(24), 5891-5898 and Nottelet et al. Biomacromolecules (2012), 13, 1544-1553.

In a second embodiment, the antibacterial agent is a quaternary ammonium of formula (VIIa):

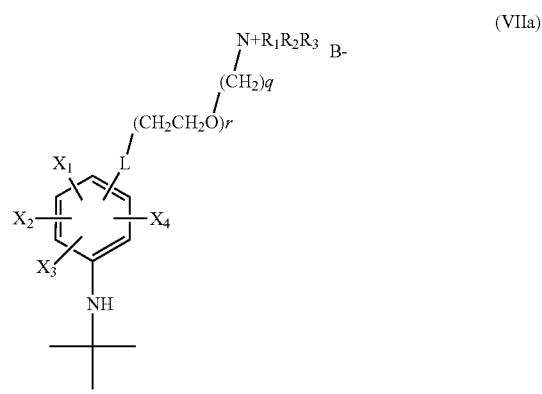

with $X_1$ to $X_4$ and L as defined above, q an integer from between 0 and 10, preferably between 1 and 8, r an integer from between 0 and 3000, preferably between 0 and 500, $R^1$, $R^2$ each independently selected from a hydrogen atom or a $C_1$-$C_6$ alkyl group, $R^3$ independently selected from a hydrogen atom or a $C_1$-$C_9$ alkyl group, and B— representing a pharmaceutically acceptable base.

For instance, L is NH, X is H, r is 0, q is 3, and $R^1$, $R^2$ and $R^3$ are each methyl and B— is bromine. In a third embodiment, the antibacterial agent is a quaternary phosphonium of formula (VIIb):

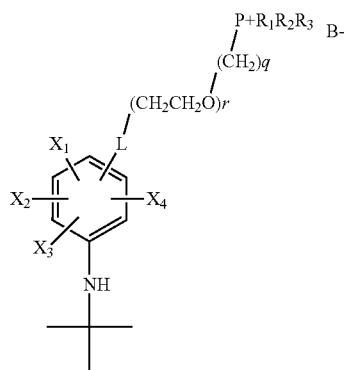

(VIIb)

with $X_1$ to $X_4$ and L as defined above,
q an integer from between 0 and X, preferably between 1 and 8,
r an integer from between 0 and 3000, preferably between 0 and 500,
$R^1$, $R^2$ each independently selected from a hydrogen atom or a $C_1$-$C_6$ alkyl group, $R^3$ independently selected from a hydrogen atom or a $C_1$-$C_9$ alkyl group,
and B— representing a pharmaceutically acceptable base.

In a fourth embodiment, the antibacterial agent is a quaternary pyridinium of formula (VIIc)

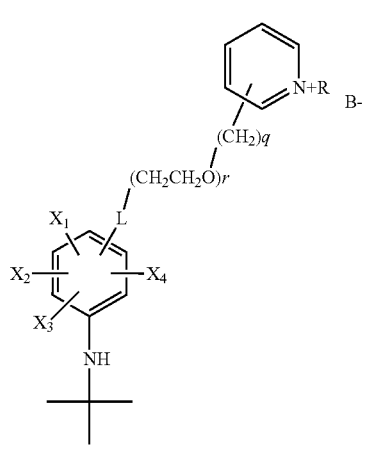

(VIIc)

with $X_1$ to $X_4$ and L as defined above,
q an integer from between 0 and 10, preferably between 1 and 8,
r an integer from between 0 and 3000, preferably between 0 and 500,
R selected from a hydrogen atom or a $C_1$-$C_6$ alkyl group, and
B— representing a pharmaceutically acceptable base.

In a fifth embodiment, the antibacterial agent is an antibacterial peptide of 25 amino acids or less (preferably 20 amino-acids or less) and preferably selected from a polyarginine (such as octaarginine Arg8), aurein and polymyxin B, and comprises a pending group of formula (VI) as defined above.

Preferably, in this fifth embodiment, the antibacterial agent is selected from a polyarginine (such as octaarginine Arg8) comprising one pending photoactive aryl-amino moiety of formula (VI) as defined above.

III.2.b. Properties-Imparting Compound Useful for Medical Imaging

In a particular embodiment, the properties-imparting compound is useful in medical imaging. In particular, the properties-imparting compound is a radio-opaque iodinated contrast agent, a complex of a lanthanide (in particular with a linear or macrocyclic polyamine), or a fluorescent compound, including a near-infrared fluorescent compound.

Radio-Opaque Compounds

In a particular embodiment, the properties-imparting compound is radiopaque.

In a particular embodiment, the radio-opaque compound may be an iodinated compound of formula (VIII):

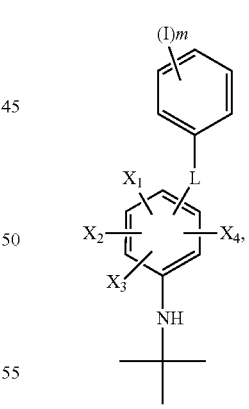

(VIII)

with $X_1$ to $X_4$ and L as defined above, and m representing 1, 2, 3 or 4.

More specifically, the radio-opaque compound may be:
an iodobenzyl derivative of formula (VIIIa)

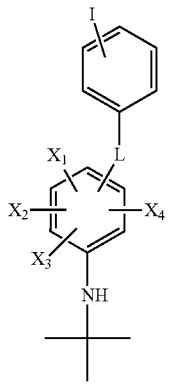
(VIIIa)

with $X_1$ to $X_4$ and L as defined above,
or a triiodobenzyl of formula (VIIIb):

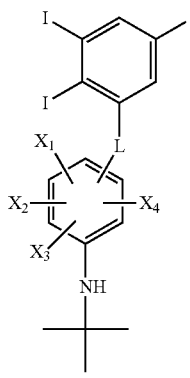
(VIIIb)

with $X_1$ to $X_4$ and L as defined above.

Preferably, $X_1$ to $X_4$ represents H.

For instance, the radio-opaque compound is a triiodobenzyl of formula (VIIIb) with $X_1$ to $X_4$ representing H and L representing —NHC(O)— or —C(O)NH—.

In another particular embodiment, the radio-opaque compound is a polymer comprising an iodinated moiety of formula

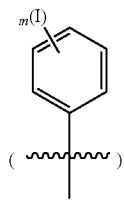

with m representing 1, 2, 3 or 4, such as an iodophenyl moiety

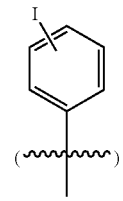

or a triiodophenyl moiety

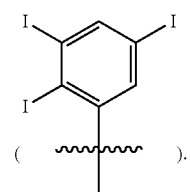 [SMILES: *c1cc(I)cc(I)c1I]

For instance, the polymer is a block or gradient copolymer of monomers of formula A1 as defined above and of monomers of formula B4a or B4b as defined above.

MRI

In a particular embodiment, the properties-imparting compound acts as a MRI contrast agent. Typically, the properties-imparting compound comprises a gadolinium complex of DOTA (1,4,7,10-tetraazacyclododecan-1,4,7,10-tetraacetic acid), DTPA (diethylenetriaminopentaacetic acid), DO3A (1,4,7,10-tetraazacyclododecan-1,4,7-triacetic acid), HPDO3A (10-(2-hydroxypropyl)-1,4,7,10-tetraazacyclododecan-1,4,7-triacetic acid), TRITA (1,4,7,10-Tetrakis(carboxymethyl)-1,4,7,10-tetraazacyclotridecane), TETA (1,4,8,11-Tetrakis(carboxymethyl)-1,4,8,11-Tetraazacyclotetradecane), BOPTA (4-carboxy-5,8,11-tris(carboxymethyl)-1-phenyl-2-oxa-5,8,11-triazatridecan-13-oic acid), NOTA (1,4,7-triazacyclononane-N,N',N44-triacetic acid), PCTA (3,6,9,15-tetraazabicyclo[9.3.1]pentadeca-1(15),11,13-triene-3,6,9-triacetic acid), DOTMA ((alpha, alpha', alpha'', alpha''')-tetramethyl-1,4,7,10-tetraazacyclododecan-1,4,7,10-tetraacetic acid), AAZTA (6-amino-6-methylperhydro-1,4-diazepinetetraacetic acid) and HOPO (1-hydroxypyridin-2-one), preferably DTPA, DOTA, NOTA, DO3A and PCTA, even more preferably DTPA or DOTA.

It may in particular be of formula (IX):

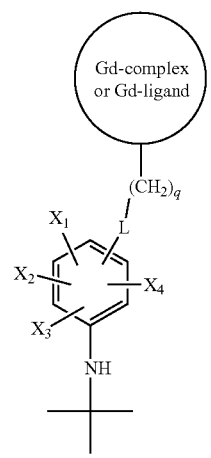
(IX)

with $X_1$ to $X_4$ and L as defined above,
q an integer from between 0 and 10, preferably between 1 and 8, more preferably 2, and Gd-complex a gadolinium complex in particular as listed above, preferably DTPA, DOTA, NOTA, DO3A and PCTA, even more preferably DTPA or DOTA.

In a particular embodiment, the properties-imparting compound is of formula (IXa) or (IXb):

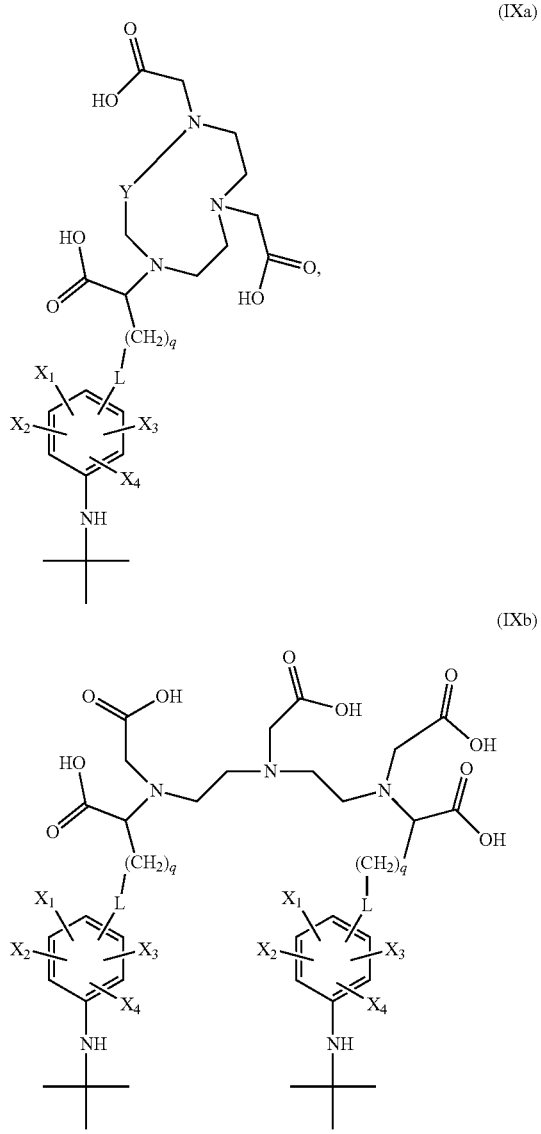

with $X_1$ to $X_4$ and L as defined above,
q an integer from between 1 and 10, preferably between 2 and 8, more preferably 2, and
Y selected from a bond, a —CH$_2$N(CH$_2$CH$_2$COOH)CH$_2$CH$_2$— group, or a

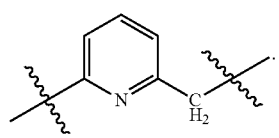 [SMILES: *Cc1cccc(*)n1]

In formulae (IX) and (IXa), preferably, X is H and L is a —NHC(O)— or a —C(O)NH— group.

Where appropriate, the compounds of formulae (IX), (IXa) or (IXb) are preferably used as a salt with a pharmaceutically acceptable base, such as NaOH or methylglucamine.

It may also be a block- or gradient-copolymer of monomers A1 as defined above and of monomers (B5), (B5a), (B5b) and (B5c) as defined above, wherein "Gd-complex or ligand" is a gadolinium ligand, in particular as listed above, preferably DTPA, DOTA, NOTA, DO3A and PCTA, even more preferably DTPA or DOTA, complexed with gadolinium. Where appropriate, it is preferably used as a salt with a pharmaceutically acceptable base, such as NaOH or methylglucamine.

Alternatively, the properties-imparting compound may comprise a gadolinium complex of a macromolecular ligand such as PCL, poly(meth)acrylate, poly(5-Amino-δ-valerolactone) copolymers, in particular as described in patent applications WO2013084204A1 and WO2011004332.

In this embodiment, the properties-imparting compound may in particular be a copolymer containing a propargyl pending groups such as described for instance in WO 2011/004332 or WO 2013/084204, and further including the aryl-amino moiety of formula (VI) as defined above.

Fluorescence and IR Imaging

In a particular embodiment, the properties-imparting compound is useful as a contrast agent for fluorescence or near IR imaging.

In a first embodiment, the properties-imparting compound is a rhodamine derivative of formula (Xa):

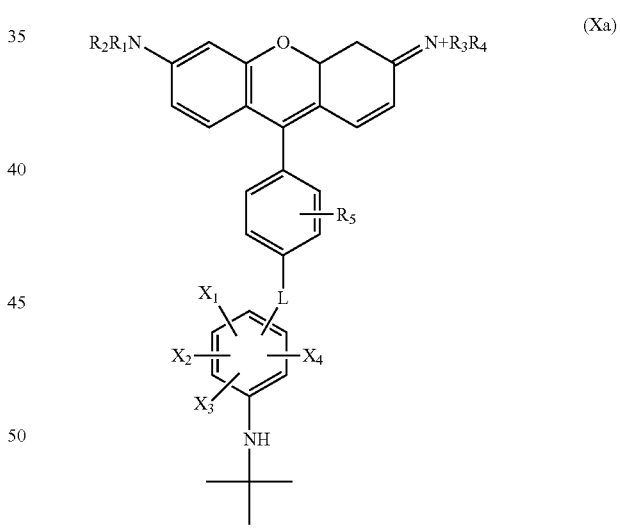

with
$X_1$ to $X_4$ and L as defined above,
$R^1$, $R^2$, $R^3$ and $R^4$ each independently selected from a hydrogen atom or a $C_1$-$C_6$ alkyl group, and $R^5$ selected from a hydrogen atom, a COOH or a C(O)O$C_1$-$C_6$ alkyl group.

In this first embodiment, preferably L is —NHC(S)NH— and X is H. Advantageously, $R^5$ is COOH. Preferably, $R^1$, $R^2$, $R^3$ and $R^4$ are each ethyl (CH$_2$CH$_3$).

Typically, in this embodiment, compound (Xa) is a salt with B$^-$, wherein B$^-$ is a pharmaceutically acceptable anion, such as a halogen anion, typically Cl$^-$ or Br$^-$, preferably Cl$^-$.

In a second embodiment, the properties-imparting compound is a cyanin derivative of formula (Xb):

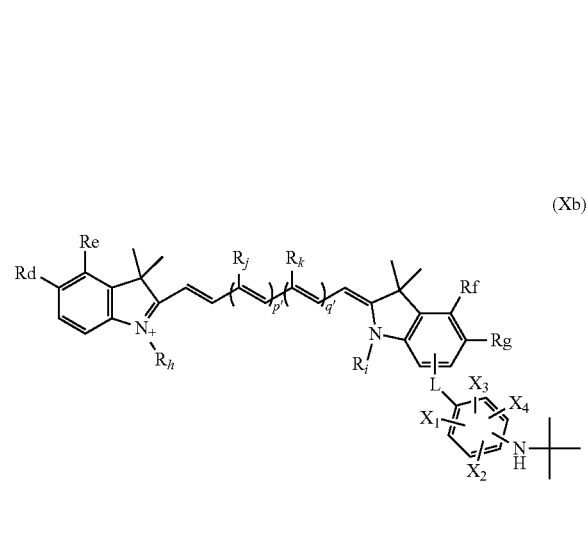

with $X_1$ to $X_4$ and L as defined above, p' being 0 or 1, q' being 0 or 1 if p' is 0 then $R_k$ is H, if q' is 0 then $R_j$ is H, if p' is 1 and q' is 1, then $R_j$ and $R_k$ are both H or taken together, form a —$CH_2CH_2CH_2$— bridging group, $R_d$ is selected from H and $SO_3Na$, and $R_e$ is H or taken together, $R_d$ and $R_e$ form a —$CH_2CH_2CH_2$— or —CHCHCH— bridging group, $R_g$ is selected from H and $SO_3Na$, and $R_f$ is H, or taken together, $R_f$ and $R_g$ form a —$CH_2CH_2CH_2$— or —CHCHCH— bridging group, $R_h$ being selected from a ($C_1$-$C_6$)alkyl group, optionally substituted with a $SO_3$— or a COOH group, preferably on the last carbon atom, $R_i$ being selected from a ($C_1$-$C_6$)alkyl group, optionally substituted with a $SO_3Na$ or a COOH group, preferably on the last carbon atom.

Preferably, in this embodiment, taken together, $R_d$ and $R_e$ form a —CHCHCH— bridging group, and $R_f$ and $R_g$ form —CHCHCH— bridging group. Then, $R_h$ is advantageously a $C_4$-alkyl group substituted with a $SO_3$— group on the last carbon (i.e. a group —$(CH_2)_5$—$SO_3$—), and $R_i$ is advantageously a $C_4$-alkyl group substituted with a $SO_3Na$ group on the last carbon (i.e. a group —$(CH_2)_5$—$SO_3Na$). In this embodiment, $R_j$ and $R_k$ are preferably both H and p' and q' are preferably both 1.

Typically, in this embodiment, compound (Xb) is a salt with B⁻, wherein B⁻ is a pharmaceutically acceptable anion, such as a halogen anion, typically Cl⁻ or Br⁻, preferably Cl⁻.

In a third embodiment, the properties-imparting compound is a fluorescein derivative of formula (Xc):

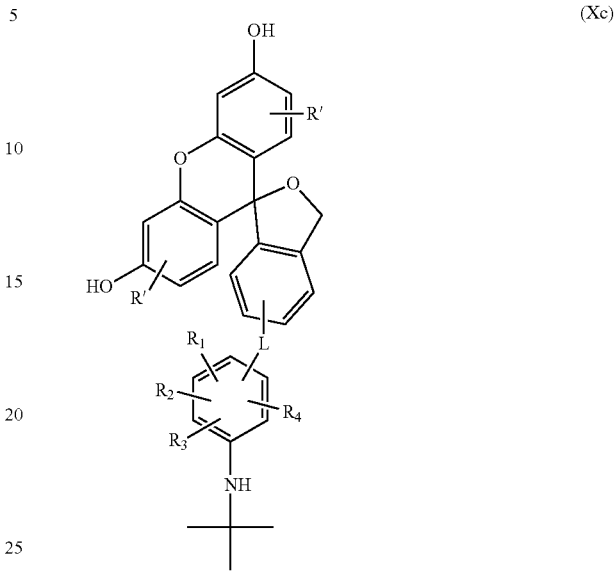

with $X_1$ to $X_4$ and L as defined above, and R' representing H, or a —$CH_2CH_2COOH$ or —CH=CHCOOH group.

Preferably, in this embodiment, L is —NHC(S)NH— and X is H. Advantageously, R' is H.

For fluorescence imaging, the rhodamine derivatives of formula (Xa) as defined above are preferably used.

For near IR imaging, the fluoresceine derivative of formula (Xc) or the cyanin derivative of formula (Xb) as defined above are preferably used.

III.3. Grafted Substrates Obtainable by the Method of the Invention

The surface-modified polymeric (implantable) substrates of the invention are obtainable by the method of the invention.

III.4. Miscellaneous

The present invention encompasses all combinations of the particular and preferred embodiment described above in connection with the substrate of the invention.

IV. Medical Device

The present invention further relates to a medical device comprising a surface-modified implantable substrate of the invention.

In particular, the medical device of the invention is suitable as implant (in particular as implantable supporting device for soft tissues), as catheter, implantable mesh (in particular surgical mesh), implantable membranes, stents, drains, vascular grafts, implantable guides and implantable tissue (such as ligament prostheses).

The medical devices of the invention are of particular interest in particular when they include a surface-modified substrate containing radiopaque compounds or compounds visible in medical imaging. Indeed, it will then be possible to follow bio-integration and stability of the medical device thanks to non-invasive medical imaging techniques, which is not possible up to date in the case of implantable supporting device for soft tissues. Indeed, such implantable supporting devices are not visible even with echography in some cases.

In addition, it will be possible to include a reference number on the medical device, which will be readable thanks to non-invasive medical imaging techniques, so that it will be easily identifiable if needs be (through CE number, batch number etc).

In addition, it is noteworthy that the medical devices of the invention including a surface-modified substrate grafted with gadolinium complexes require over 10 000 less gadolinium than usual contrast agent injections to obtain a god contrasted image of the device.

V. Non Medical Uses of the Surface-Modified Polymeric Substrates of the Invention The present invention further relates to non-therapeutic, or more generally to non-medical uses of the surface-modified polymeric substrates of the invention.

In particular, substrates grafted with antifouling and/or antibacterial compounds find applications in various fields of technology. For instance, such substrates are useful in the manufacture of materials with mist-suppressing or anti-fogging properties, in particular for vehicles, such as cars (including motorbikes, lorries, i.e. in the automotive industry), trains, boats. . . . They may also be useful in the building industry or in the textile industry.

EXAMPLES

The present invention will be illustrated through the following examples, which are not to be construed as limiting the scope of the invention in any way.

1. Functionalization with 4-Azidoaniline Modified Gd-Diethylene Triamine Pentaacetic Acid (Gd-DTPA-biN$_3$) Complex Clip-Synthesis:

Under argon-atmosphere 2.2 eq 4-Azidoaniline hydrochloride were dissolved in anhydrous DMF and 2.2 eq TEA. 1 eq diethylene triamine pentaacetic dianhydride was added to the clear solution and the reaction mixture heated to 50° C. for 2 h and left stirring at RT over night in the dark and under Ar-atmosphere. The solvent was removed under high vacuum and the residue suspended in MeOH/EtOH and precipitated in cold diethylether/chloroform (50/50; v/v). Precipitation was repeated two more times, followed by dissolution in H$_2$O and lyophilization to obtain DTPA-biN$_3$ as a yellowish powder.

1 eq of DTPA-biN$_3$ and 10 eq pyridine were dissolved in H$_2$O and shaken for 30 min at 40° C. 2 eq GdCl3.6H$_2$O were added and the reaction mixture shaken over night at 40° C. The precipitated product was dissolved in an access of H$_2$O and treated with Chelex 100 to remove free Gd. The treatment was repeated until no further free Gd was detected with the MTB-test.

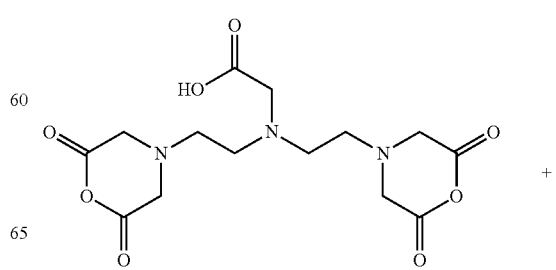

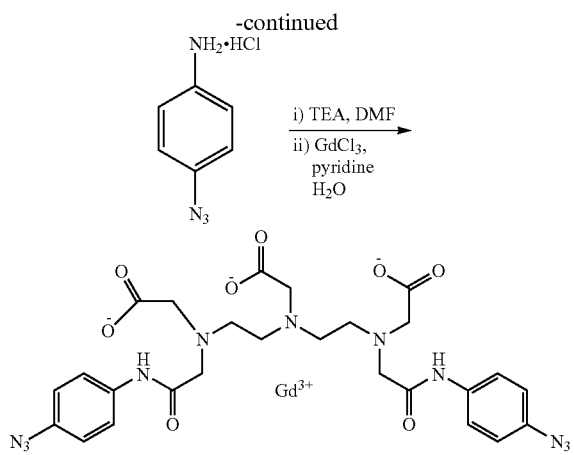

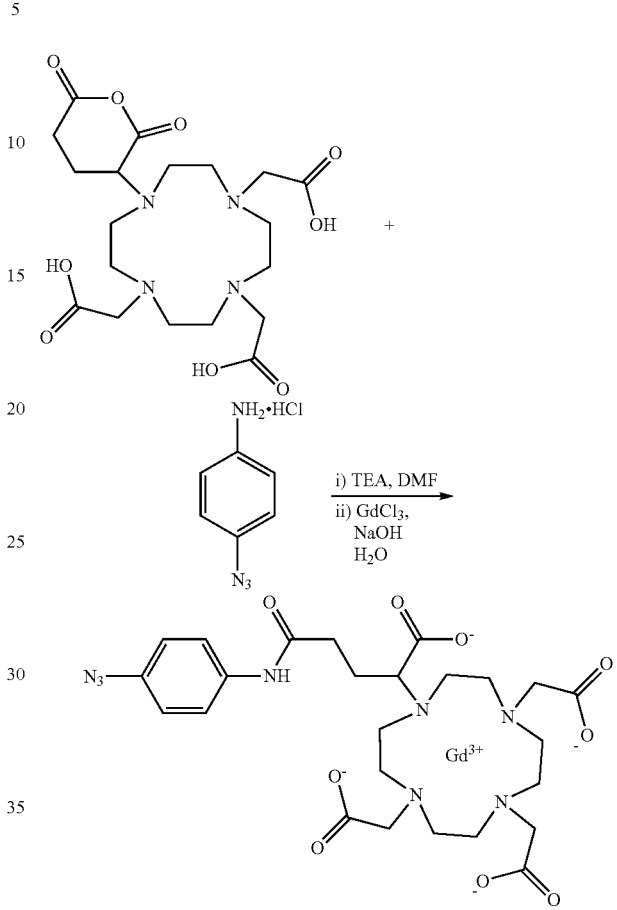

Surface-Functionalization:

Clean polymer (e.g. PLA, PLA-Pluronic-PLA, PLGA, PCL, PP) surface (film, mesh, pressed pellet) was covered with 1-5 g/L clip in degassed MeOH and irradiated for 5-30 min at 254 nm. Subsequently the surface was rinsed with H$_2$O and EtOH.

MRI Imaging

Material.

Bruker 7T BIOSPEC 70/20, "mini-imaging" configuration (gradient BGA12 675 mt/m, resonator "bird cage" 35 mm). After a set of marker gradient echo sequences, a spin3D echo sequence was acquired (FOV 3*3*1 cm matrix 128*128*48, TR=3000 ms, TE=8 ms (TEeff=16), RF=8, acquisition time of 0:51) with an inversion delay of 1300 ms.

MGE 3D sequences with TR/TE 110/3 ms and angles of 75, 30 and 15° were acquired.

Figure 1:
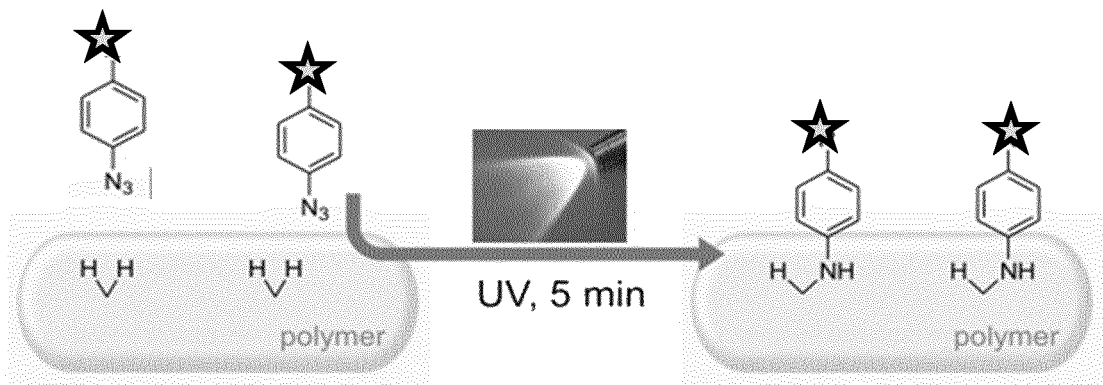
FIG. 1. Scheme depicting the grafting method of the invention, using clip chemistry. The stars attached to the aryl-azide and aryl-amino moieties represent the properties-imparting compounds of the invention before and after grafting.
Figure 2:
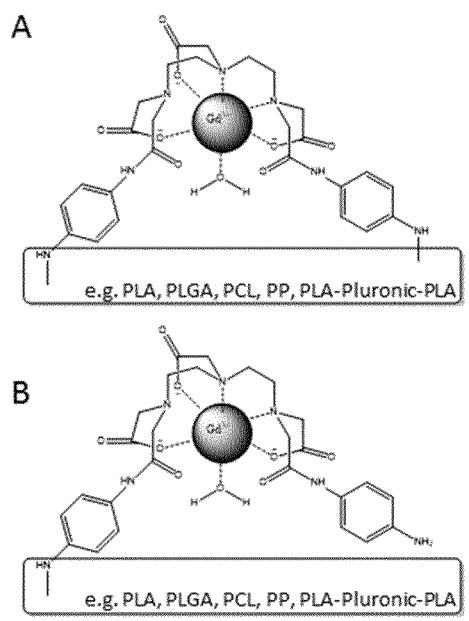
FIG. 2. A,B: Possible ways of attachment of Gd-DTPA-biN3 after UV-irradiation on various polymer surfaces. C: Visibility of PP-mesh via MRI after UV treatment with Gd-DTPA-biN3.
Figure 2:
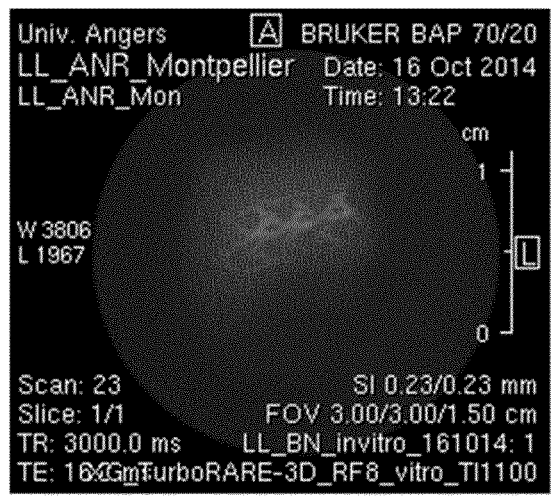
Figure 9:
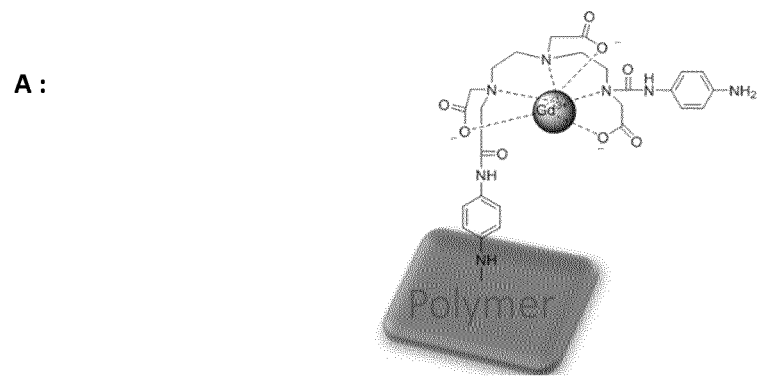
FIG. 9. A: schematic representation of the substrate-modified films. B: MRI imaging of various polyester substrates (from left to right: PCL, PLA and PLGA) grafted with a DTPA aryl-amide moiety (7T, spin echo sequence with inversion, T1=1300 ms). C. MRI imaging of various polyester substrates grafted with a DTPA aryl-amide moiety (7T, spin echo sequence with inversion, T1=1300 ms), at t=0 and after 2 months incubation in a PBS medium (pH=7.4) at 37° C.
Figure 9:
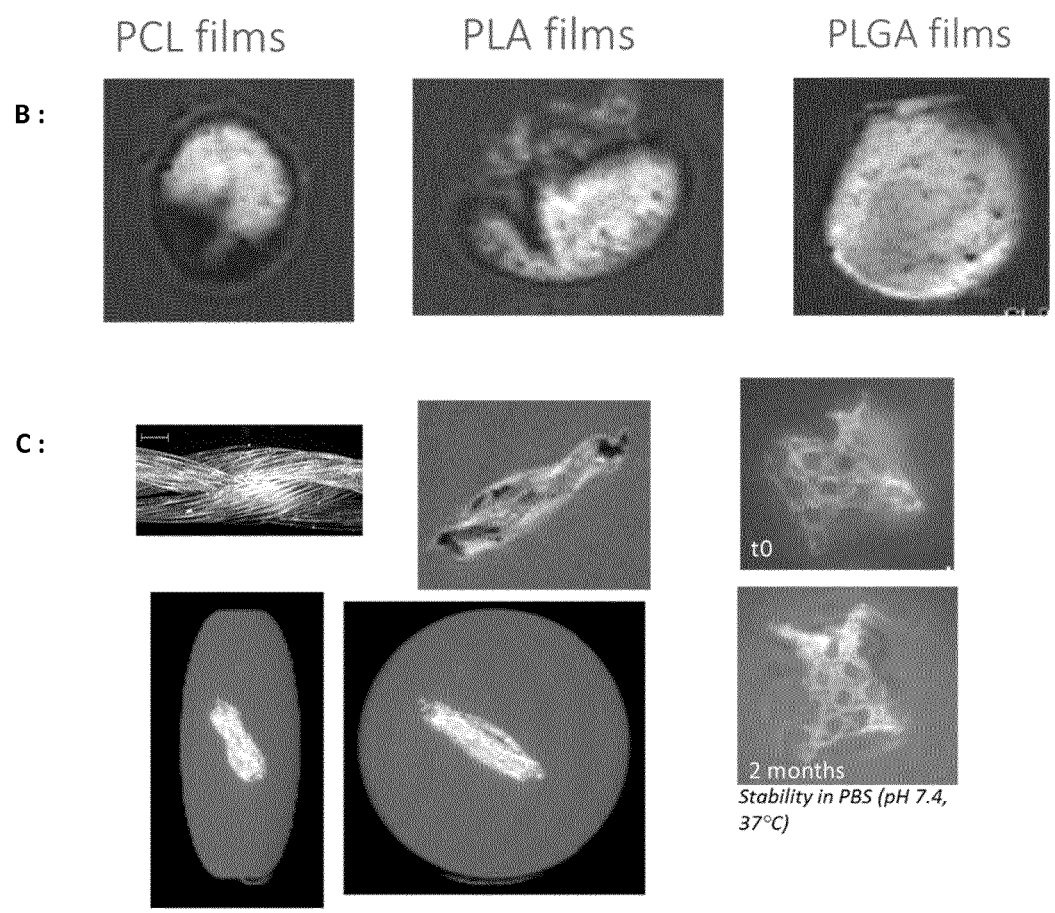

Assumptions as to the binding of the nitrene to the polymeric substrate are presented in FIGS. 2 and 9A, as well as the visibility by MRI measurements (FIGS. 2C and 9B).

MRI imaging on PCL, PLA and PLGA films (substrates), the surface of which has been grafted with the DTPA-N3 described above is described on FIG. 9B. These images were obtained after submitting the surface-modified substrates to a spin echo sequence with inversion (7T, T1=1300 ms).

Stability of MRI-visibility for PP modified meshes after 2 months in saline phosphate buffer (pH 7.4, 37° C.) is shown in FIG. 9C. Surface-modified substrates with a thread-like shape were also successfully tested for stability: the image obtained after two months in a PBS medium (pH=7.4) at 37° C. does not show any image degradation (see FIG. 9C).

2. Functionalization with 4-Azidoaniline Modified Gd-2-(4,7,10-triacetic acid)-1,4,7,10-tetraazacyclododecan-1-yl) pentanedioic Acid, (Gd-DOTA-N$_3$) Complex Clip-Synthesis:

In an evacuated schlenk-flask 1 eq 4-azidoaniline hydrochloride were dissolved in anhydrous DMF. 1.2 eq TEA and 1.2 eq DOTA-GA anhydride (2,2',2''-(10-(2,6-dioxotetrahydro-2H-pyran-3-yl)-1,4,7,10-tetraazacyclododecane-1,4,7-triyl)triacetic acid) were added. The reaction mixture was stirred for 3 h at 45° C. and continued to be stirred at RT over night. The solvent was removed under high vacuum and mild heating. The residue was dissolved in MeOH/CHCl$_3$ (2/1; v/v) and precipitated in diethyl ether. Subsequently the precipitate was centrifuged, dried, dissolved in H$_2$O and lyophilized to obtain DOTA-N$_3$ as a yellow-brownish powder.

1 eq of DOTA-N$_3$ and 10 eq pyridine (or NaOH) were dissolved in H$_2$O (pH~6.5). 2 eq GdCl3.6H$_2$O were added and the reaction mixture shaken for 2 h to 15 h at 40-60° C. The solution was diluted with more H$_2$O and treated with Chelex 100 to remove free Gd. The treatment was repeated until no further free Gd was detected with the MTB-test.

Surface-Functionalization:

Clean polymer (e.g. PLA, PLA-Pluronic-PLA, PLGA, PCL, PP, PEEK, PU) surfaces (film, mesh, pellet) heated to temperatures from RT to 80° C. were covered with 1-20 g/L clip in degassed MeOH (e.g. by spraying), air dried and irradiated for 5-10 min at 254 nm. Subsequently the surface was rinsed with H$_2$O and EtOH. The irradiation step was optionally repeated up to 5 time to increase surface coverage. Final purification in H$_2$O for 20 min in ultrasonic bath.

Implantation in Rats and Imaging

Control (untreated) and surface-modified surgical meshes (1 cm×2 cm) are desinfected using 70% ethanol and are sterilized by UV irradiation.

4 female rats are implanted with one control and one surgical mesh (2 meshes per rat). The prostheses are implanted in the dorsal muscle lodges. The control mesh is implanted in the left lodge, while the surface-modified mesh is implanted in the right lodge.

MRI of the implanted rats are then carried out, using Spin Echo and Gradient Echo sequences at 9T, acquiring data for 30-40 minutes. The experiments were carried out on the BioNanoNMRI small animal MRI platform of the Universite de Montpellier.

Figure 3:
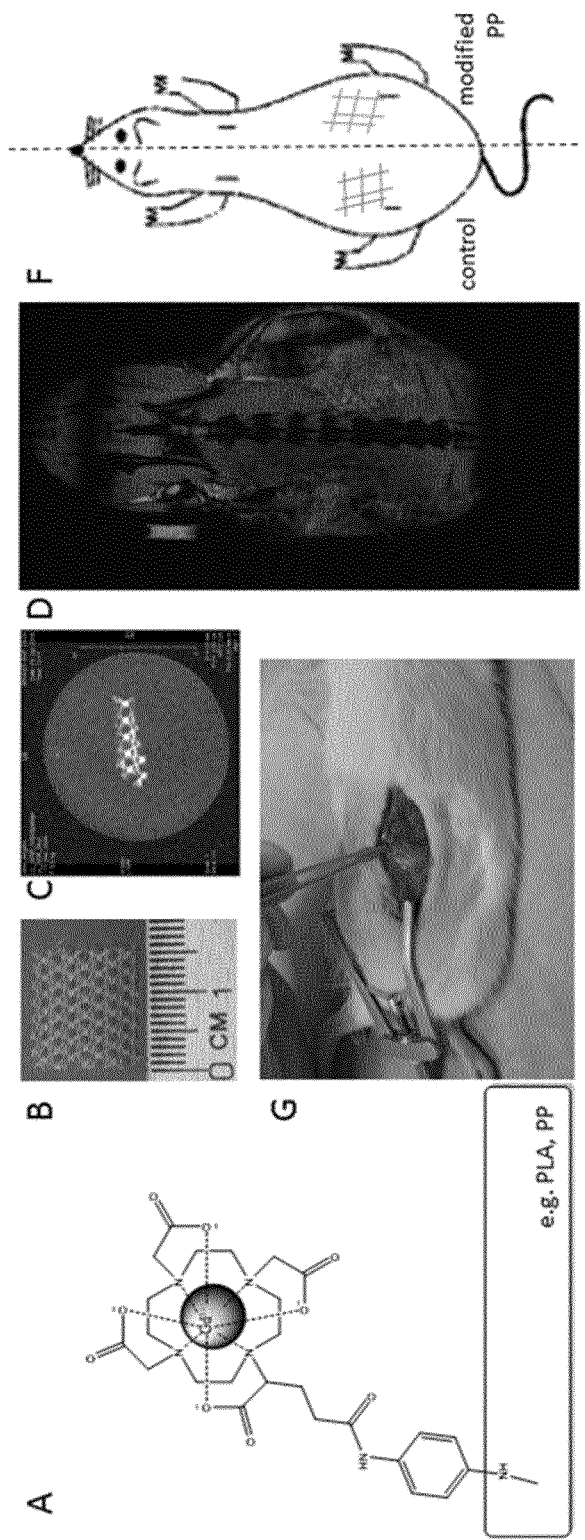
FIG. 3. A: Scheme of Gd-DOTA-N3 attachment on various polymer surfaces. B: Typical PP-mesh used for functionalization. C: Detection of PP-mesh via MRI after UV-treatment with Gd-DOTA-N3 D: Visibility of Gd-DOTA-N3 functionalized PP-mesh in vivo in rats. F: Position of untreated and treated PP-mesh in rat. G: Image of implantation side of PP-mesh in rat.

A scheme depicting the structure of the surface-modified substrate thus obtained is presented in FIG. 3 (A). FIG. 3 also shows a surgical mesh whose surface has been modified as above (B), and its visibility in MRI (B). The surface-modified mesh of the invention was implanted in a mouse (G), and the visibility of the implanted surgical mesh of the invention in vivo by MRI (D, F).

Biocompatibility of Modified Surfaces (MRI)

a) Cytotoxicity Assay Via Direct Contact Method

L929 cells (Sigma-Aldrich) were seeded at $1.7 \cdot 10^4$ cells per well in a 24-well plate and allowed to attach overnight under appropriate atmosphere. Polymers PLA and PP with and without Gadolinium complex were cut in order to cover about 1/10 of the well surface (as mentioned in ISO 10993-5). Decontamination was realized: first step with ethanol 70% followed by 3 washing step with PBS-penicillin/streptomycin 10% and then PBS only.

The cell growth medium was replaced and the decontaminated polymer films were placed on the top. After 48 h incubation at 37° C. 5% $CO_2$, polymers were removed and cell viability was assessed by using Prestoblue® cell viability assay (Invitrogen, A13261) according to manufacturer's instructions. Briefly, Prestoblue® was added at 10% in growth medium and the fluorescence at 590 nm was measured after 45 minutes incubation. Wells without addition of polymers films are used as controls (n=4).

b) Cell Proliferation Assay

Polymers PLA and PP with and without Gadolinium complex were cut in order to cover 24-well plate surfaces (1.9 $cm^2$). Polymer discs were swabbed with paper soaked with ethanol 70% and then rinse with 3 baths of PBS-penicillin/streptomycin 10% and then with PBS only.

L929 cells (Sigma-Aldrich) were seeded on top of polymer (in the center) held by ring, at $2.10^5$ cells per well in a 24-well non-treated plate and incubated under appropriate atmosphere for about 2 h, time for cells to adhere. Then after washing non-adherent cells with PBS, fresh growth medium was added. Cell proliferation at 24 h, 48 h and 120 h was assessed by using Prestoblue® cell viability assay (Invitrogen, A13261) according to manufacturer's instructions. Wells without addition of polymers films are used as controls (n=5).

Figure 10:
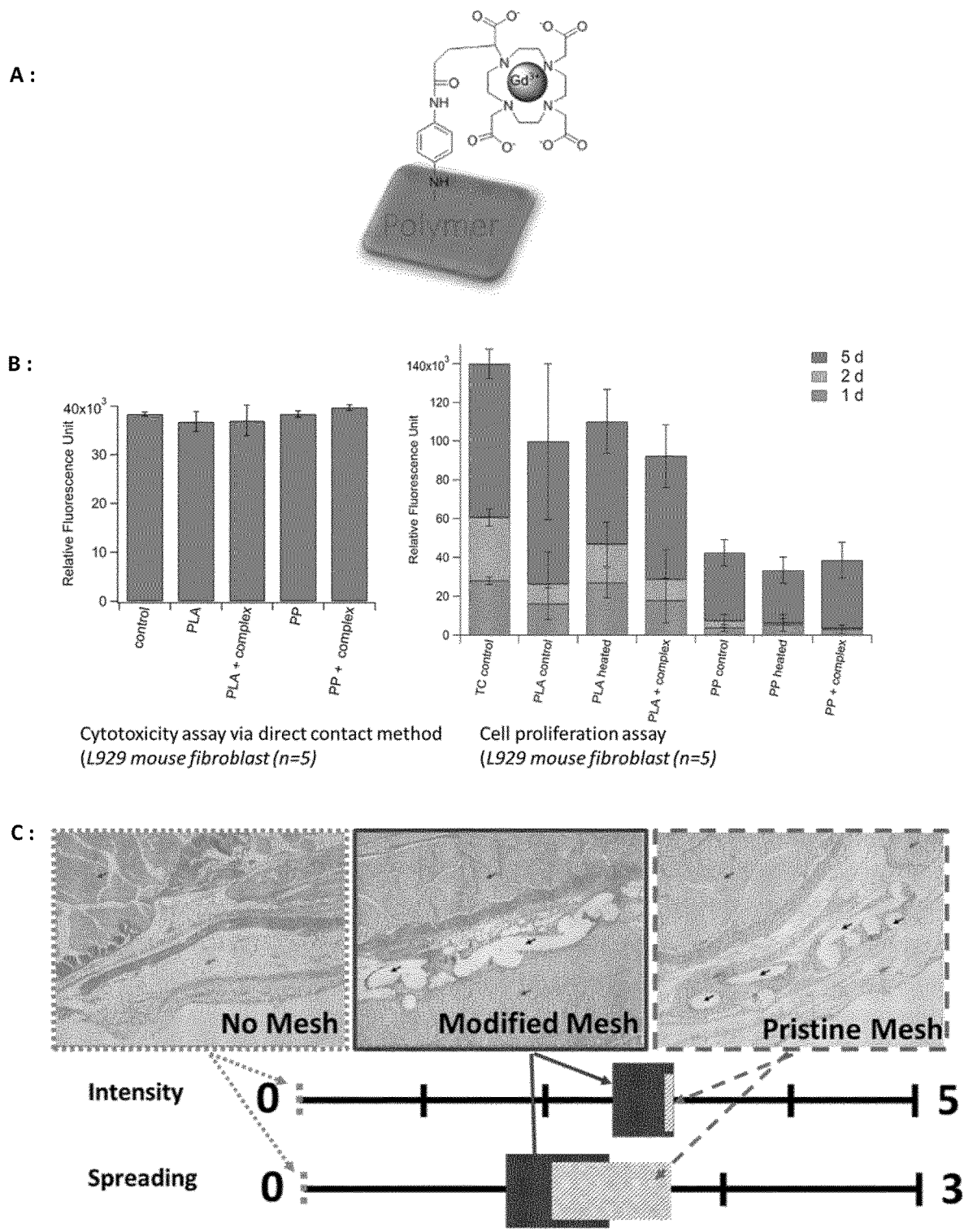
FIG. 10. A: schematic representation of the substrate-modified films. B: biocompatibility assessment of substrates grafted with a DOTA aryl-amide moiety with a cytotoxicity assay by direct contact (left) and with a cell proliferation assay (right) on L929 mouse fibroblasts (n=5). C. Histological evaluation of the inflammatory response of substrates grafted with a DOTA aryl-amide moiety. Histological section (HES, ×5) with muscle, muscle tissues, fat tissues, mesh, inflammation, fibrosis (top row) and grading of inflammation in implanted rats (n=4) (bottom row).

The above in vitro biocompatibility tests, the results of which are summarized in FIG. 10B, demonstrate that the method of the invention leads to non-toxic materials.

Histological Evaluation of the Inflammatory Response

Meshes were implanted into back muscle tissue of 4 rats. Each rat received modified (Gadolinium complex) and no modified meshes on the other side. Implant specimens were recovered after 1 month implantation and were fixed with 10% formalin, paraffin-embedded, sectioned, and stained with hematoxylin-eosin-safran HES (RHEM platform, Montpellier). Lesion intensity (i) and spreading (d) were graded by experienced pathologist of RHEM technical facilities. Lesion intensity graded from i0 (no lesion) to i4 (severe) according to the presence of inflammatory zones. Lesion spreading graded from d0 (no lesion) to d2 (peripheral distribution). Results were compared with one control rat (without meshes implantation).

This in vivo biocompatibility test, the results of which are summarized in FIG. 10C, demonstrate that the inflammation observed with modified meshes (results depicted by the plain squares) is due to surgery rather than to the surface modification of the material: the intensity of the inflammatory response as well as its spreading are less than or equivalent to those observed with unmodified (i.e. pristine) meshes (see results represented by the dotted squares).

3. Functionalization with 4-Azidoaniline Modified Rhodamine B

Clip-Synthesis:

1.2 eq Rhodamine B isothiocyanate were dissolved in anhydrous DMF. 2 eq DIPEA and 1 eq 4-azidoaniline hydrochloride were added and the reaction mixture was shaken for at least 3 d at 40° C. The crude product was purified via Sephadex LH20 column (MeOH as eluent).

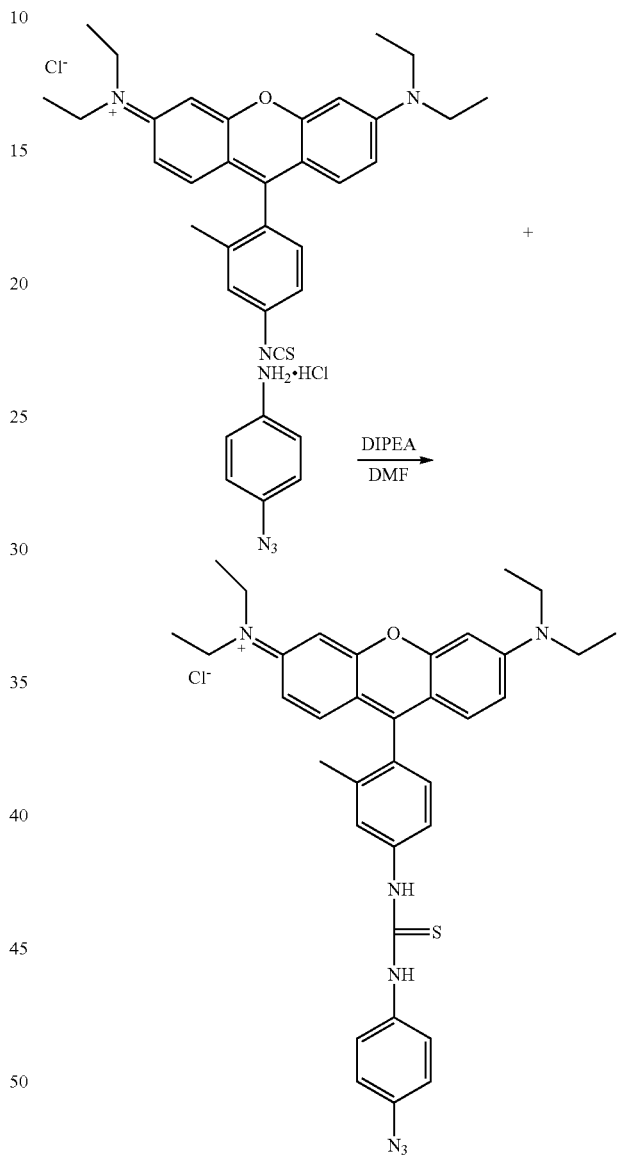

Surface-Functionalization:

Clean polymer (e.g. PLA, PP) surface (e.g. film, pressed pellet) was covered with 1-20 g/L clip in degassed MeOH and irradiated for 1-20 min at 254 nm. Subsequently the surfaces were rinsed with $H_2O$ and EtOH.

Fluorescence Measurements

Material.

Figure 4:
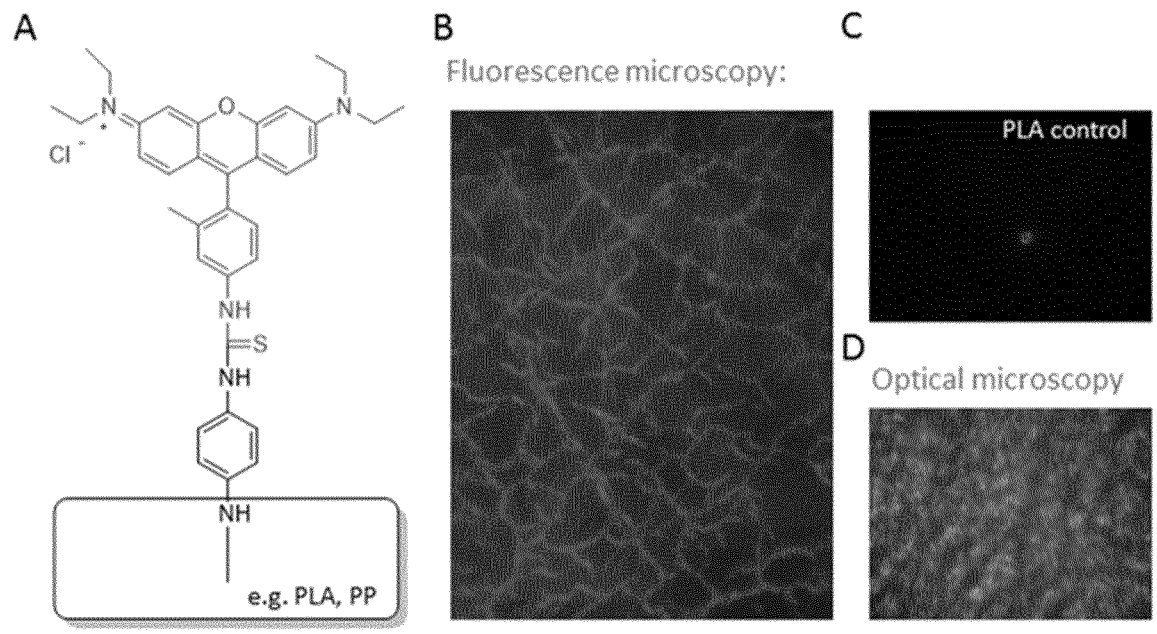
FIG. 4. A: Scheme of clip-modified Rhodamine B attached to polymer surface after UV irradiation. B,C: Fluorescence images of PLA treated with clip-modified Rhodamine B (B) and untreated PLA (C). D:PLA surface visualized with optical microscopy.

Leica fluorescence microscope, 20× magnified, green excitation wavelength (555 nm). A scheme depicting the structure of a surface-modified PLA substrate thus obtained is presented in FIG. 4 (A). FIG. 4 also shows fluorescence images and optical microscopy of the fluorescent surface-modified PLA substrate.

4. Functionalization with 4-Azidoaniline Initiated Polysarcosine, ω-Gd-DTPA Terminated Clip-Synthesis:

Sarcosine-N-Carboxyanhydride.

First, 1 eq sarcosine were freshly grounded and dried for 1.5 h under high vacuum. Subsequently the powder was dissolved in anhydrous THF, 1.3 eq limonene, 2 eq diphosgene were added slowly under a steady flow of argon. The reaction mixture was heated to 65° C. for 2 h. After cooling to room temperature the reaction mixture was flushed for another 3 h with argon into two gas washing bottles filled with aqueous 20% NaOH solution. Next, the solvent was removed under vacuum until a yellow solid remained, which was then dissolved in dry THF. After addition of 20 mL petrolether the suspension was vigorously stirred for 30 min while cooled with an ice-bath. The precipitate was allowed to settle for 4 h under continued cooling. The clear supernatant was removed carefully with a syringe under argon atmosphere. The procedure was repeated one more time using petrolether and allowing precipitation over night in the freezer (−20° C.). After drying the solid under high vacuum, the raw product was sublimated (95° C., <10$^{-2}$ mbar) under argon atmosphere, which yielded a white powder of sarcosine-NCA.

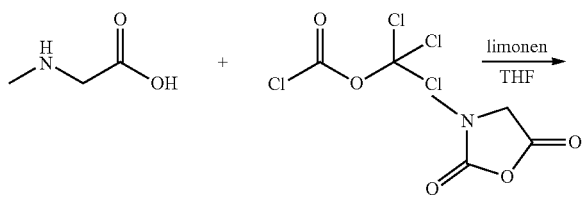

4-azidoaniline initiated polysarcosine. Initiator stock solution was prepared with 4-azido-aniline hydrochloride, TEA and dry benzonitrile. Appropriate amounts of the initiator stock solutions were added to sarcosine-NCA dissolved in dry benzonitrile (c~10 mg/mL). The reaction mixture was stirred at room temperature between 12 h and 7 d depending on the degree of polymerization. The polymer was precipitated twice in cold diethyl ether (10-20 fold of volume of polymer solution). After removal of the solvent and drying, the polymer was redissolved in H$_2$O and lyophilized. White to light yellow powders were obtained.

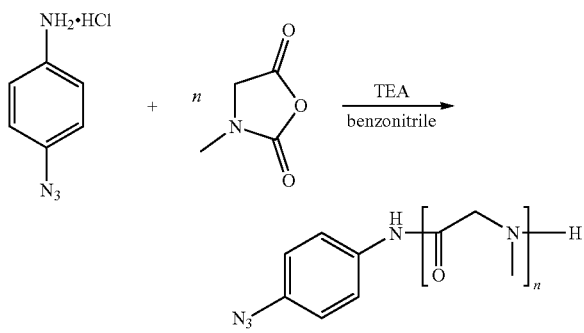

4-Azidoaniline Initiated Polysarcosine, ω-Gd-DTPA Terminated.

1 eq polysarcosine were dissolved in anhydrous DMAc. 2 eq of an acitivated form of DTPA (e.g. anhydride, thiol ester) were added (and 5 eq AgOTf together with the thiol ester) and stirred over night at RT. After removal of the solvent the residue was dissolved in CHCl$_3$ and precipitated in cold diethyl ether. Final purification was achieved via Sephadex LH20 column (MeOH as eluent).

1 eq of polymer and 10 eq pyridine were dissolved in H$_2$O and shaken for 2 h at 40° C. 2 eq GdCl3.6H$_2$O were added and the reaction mixture shaken over night at 40° C. The precipitated product was dissolved in an access of H$_2$O and treated with Chelex 100 to remove free Gd. The treatment was repeated until no further free Gd was detected with the MTB-test.

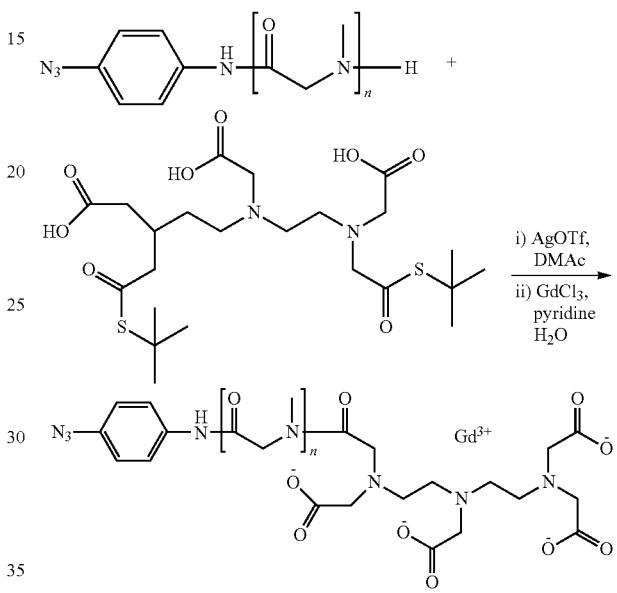

Surface-Functionalization:

Clean polymer (e.g. PLA, PCL, PP, PLGA) surface (e.g. film, mesh) was covered with 1-20 g/L polymer-clip in degassed MeOH and irradiated for 5-10 min at 254 nm. Subsequently the surfaces were rinsed with H$_2$O and EtOH.

Material.

Bruker 7T BIOSPEC 70/20, "mini-imaging" configuration (gradient BGA12 675 mt/m, resonator "bird cage" 35 mm). After a set of marker gradient echo sequences, a spin3D echo sequence was acquired (FOV 3*3*1 cm matrix 128*128*48, TR=3000 ms, TE=8 ms (TEeff=16), RF=8, acquisition time of 0:51) with an inversion delay of 1300 ms.

MGE 3D sequences with TR/TE 110/3 ms and angles of 75, 30 and 15° were acquired.

Figure 5:
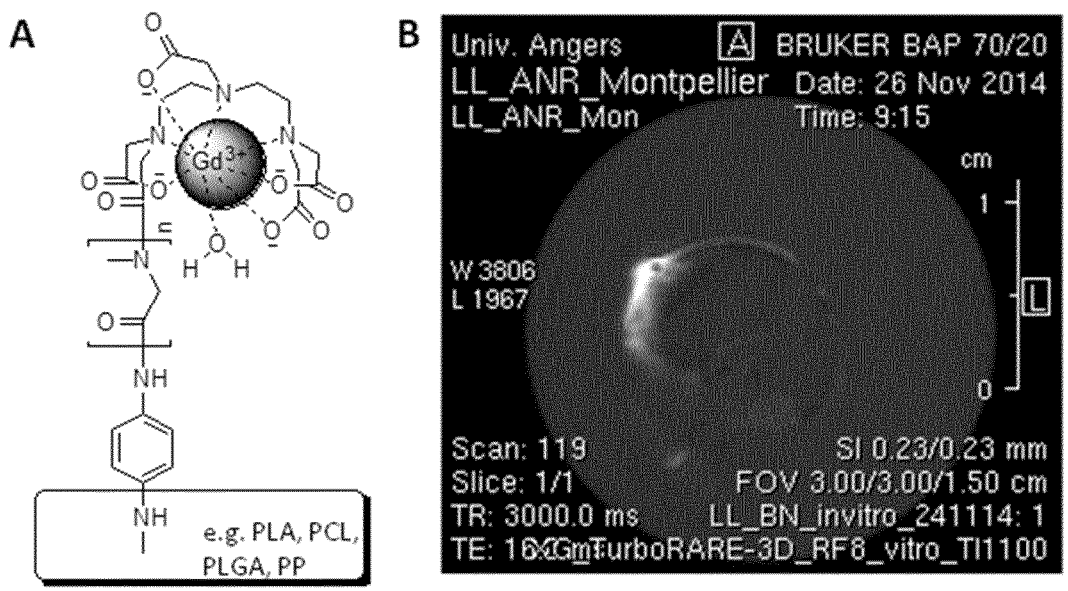
FIG. 5. A: Scheme of Gd-DTPA attached to various polymer surfaces via a clip-modified polysarcosine spacer. B: Visualization of PCL foil via MRI modified with 4-Azidoaniline initiated polysarcosine, ω-Gd-DTPA terminated.

A scheme depicting the structure of a surface-modified substrate thus obtained is presented in FIG. 5 (A). FIG. 5 also shows the MRI image of such a surface-modified PCL substrate of the invention.

5. Functionalization with 4-Azidoaniline Initiated Polysarcosine

Clip-Synthesis:

Sarcosine-N-Carboxyanhydride. Described in Chapter 4.

4-Azidoaniline Initiated Polysarcosine. Described in Chapter 4.

Surface-Functionalization:

The polymers were dissolved in degassed methanol yielding concentrations between 0.1 to 50 g/L (in general the higher the degree of polymerization the higher the concentration has to be). Polylactic acid (PLA) and polypropylene (PP) surfaces were washed prior modification for 15-30 min in methanol in ultrasonic bath. After drying for another 15 min in high vacuum, the surfaces were heated to 60° C. On the warm surfaces the polymer solution was sprayed using an airbrush. Subsequently the surfaces were irradiated for 1-30 min at 254 nm. After irradiation the surfaces were washed in methanol or ethanol for 5-10 min. The procedure was repeated up to 5 times to improve the final result. Finally the surfaces were washed with ethanol in ultrasonic bath (unless substrate not stable in ultrasonic bath, then surface was just rinsed thoroughly) and dried under vacuum.

Antifouling Effect

*S. epidermidis* ATCC49461 and *E. coli* CFT073 strains were used for these experiments.

The bacterial adhesion study was carried out using a technique adapted from Balasz et al (Biomaterials 25 (11) (2004) 2139-2151). The plates are immersed in wells containing the bacterial strain with an $OD_{600}$ (optical density at 600 nm) of 0.05, diluted in culture medium. After 1 h, the plates are removed from the wells, vigorously rinsed 3 times with sterile water, and then immersed in a neutral medium (AP or PBS). At 24 hours, the plates-adhering bacteria are recovered after vortexing and sonication in sterile saline. The bacteria were quantified by serial dilutions and plating on Mueller Hinton agar culture media. The most adherent bacteria are detached by transferring each face of the plates fifteen times on Mueller Hinton agar media. The bacteria counting is conducted after an overnight incubation at 37° C. The total adherent bacteria population is obtained by adding all cultured bacteria. The results are expressed as CFU (colony forming units). A verification of the bacteria identity is made using MALDI-TOF mass spectroscopy (Vitek-MS, BioMerieux).

Figure 6:
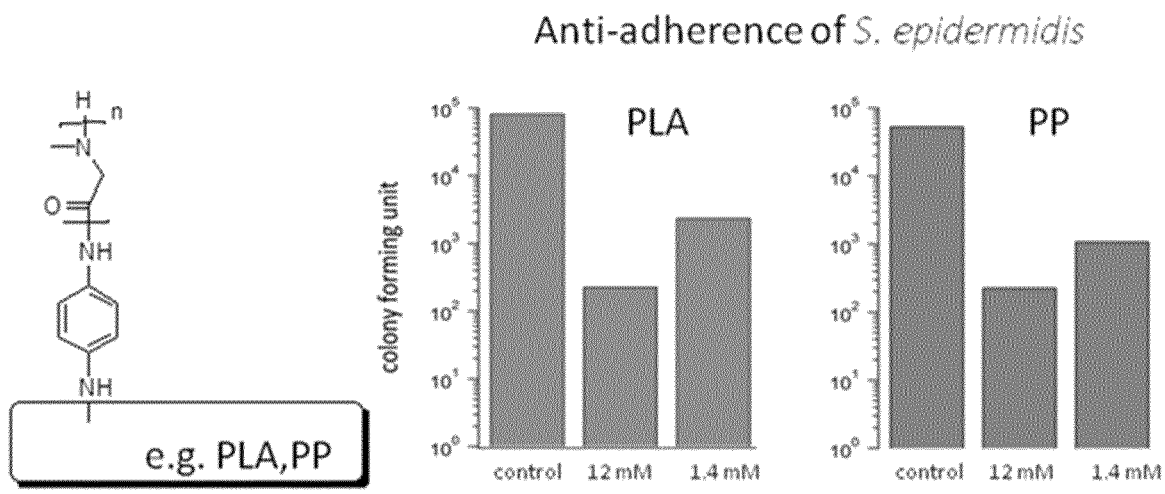
FIG. 6. Left: Scheme of polysarcosine covalently linked to polymer surface via the clip moiety. Right: Anti-adherence properties of PLA and PP surfaces untreated (control) and modified with polysarcosine.

A scheme depicting the structure of a surface-modified substrate thus obtained is presented in FIG. 6 (A). FIG. 6 also shows the anti-adherence performance of such surface-modified PLA and PP substrates of the invention, with regard to *S. epidermis*.

6. Functionalization with poly(2-methyl-2-oxazoline)-co-poly(2-(4-azidophenyl)-oxazoline) Copolymers Clip-Synthesis:

2-(4-Azidophenyl)-oxazoline. 1 eq 4-azidobenzoic acid was dried for 1 h under high vacuum. Subsequently 5 eq thionyl chloride and dry THF were added. The reaction mixture was stirred for 3 h at 70° C. under argon atmosphere. The solvent was removed under reduced pressure and the crude product crystallized in cyclohexane. After removal of the supernatant and drying 4-azido-benzoyl chloride as beige crystals were obtained.

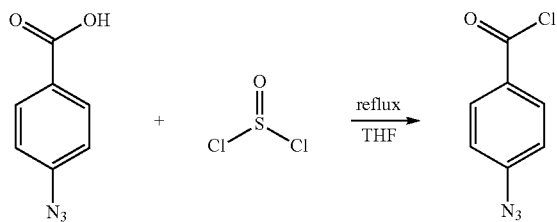

Next, 1 eq 4-azido-benzoyl chloride were dissolved in chloroform. 1.1 eq 2-bromoethylamine hydrobromide and potassium hydroxide were dissolved in $H_2O$ and cooled with an ice-bath. To the cold aqueous solution the organic solution was added and stirred for 15 min under continued cooling and for another 15 min at room temperature. The phases were separated and the organic phase washed with $H_2O$, dried with $MgSO_4$ and filtered. The solvent was removed yielding N-(2-bromoethylamine)-4-azidobenzamide as a light yellow solid.

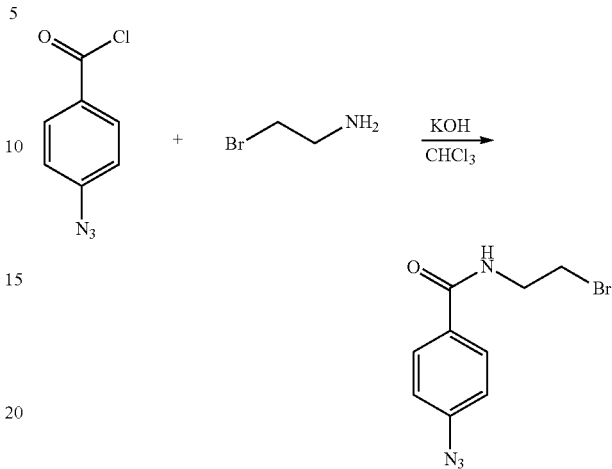

Finally, 1 eq N-(2-bromoethylamine)-4-azidobenzamide and 1.1 eq potassium hydroxide were dissolved in anhydrous methanol and stirred over night at room temperature under argon atmosphere. After removal of the solvent the residue was dissolved in dichloromethane and washed 3× with $H_2O$. Subsequently the organic phase was treated with $MgSO_4$, filtered and dried. 2-(4-azidophenyl)-oxazoline was obtained.

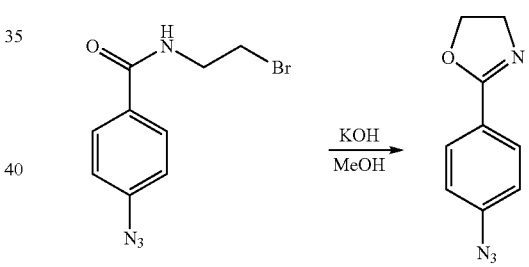

Poly(2-oxazoline).

For block-copolymers, an adequate amount of 2-(4-azidophenyl)-oxazoline (n eq) was added to an evacuated flask and dried further under high vacuum. The initiator methyl triflate (MeOTf, 1 eq), and dry acetonitrile (ACN, final monomer concentration <3 M) were also added under inert conditions. For gradient copolymers, the first block of 2-(4-azidophenyl)-oxazoline was copolymerized with a small amount 2-methyl-2-oxazoline (MeOx) to spread the functional groups within the polymer. The reaction mixture was then stirred for 3-7 d (depending on the block length) at 80° C. Next MeOx was added under argon flow to the reaction mixture. Depending on the set degree of polymerization the polymerization was carried out for another 1-7 d at 80° C. The reaction was terminated with 3 eq 1-BOC-piperazine, which was stirred for 5 h at 40° C. Subsequently an excess of potassium carbonate was added and the mixture stirred over night at room temperature. After centrifugation and filtration, the solvent was removed and the residue dissolved in a mixture of chloroform and methanol (1/2, v/v)

followed by precipitation in cold diethyl ether (10-20 fold of volume of polymer solution). After a second precipitation the polymer was dried, dissolved in H$_2$O and lyophilized. White to dark yellow powders were obtained.

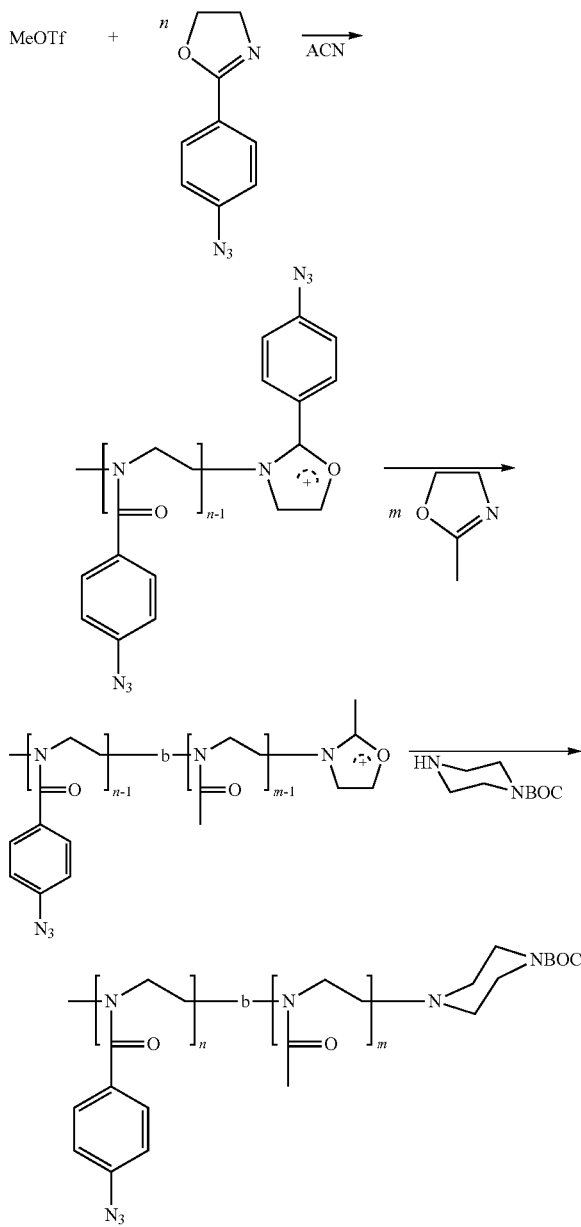

Random copolymers are obtained through a similar procedure wherein the monomers are all present during polymerization.

Figure 11:
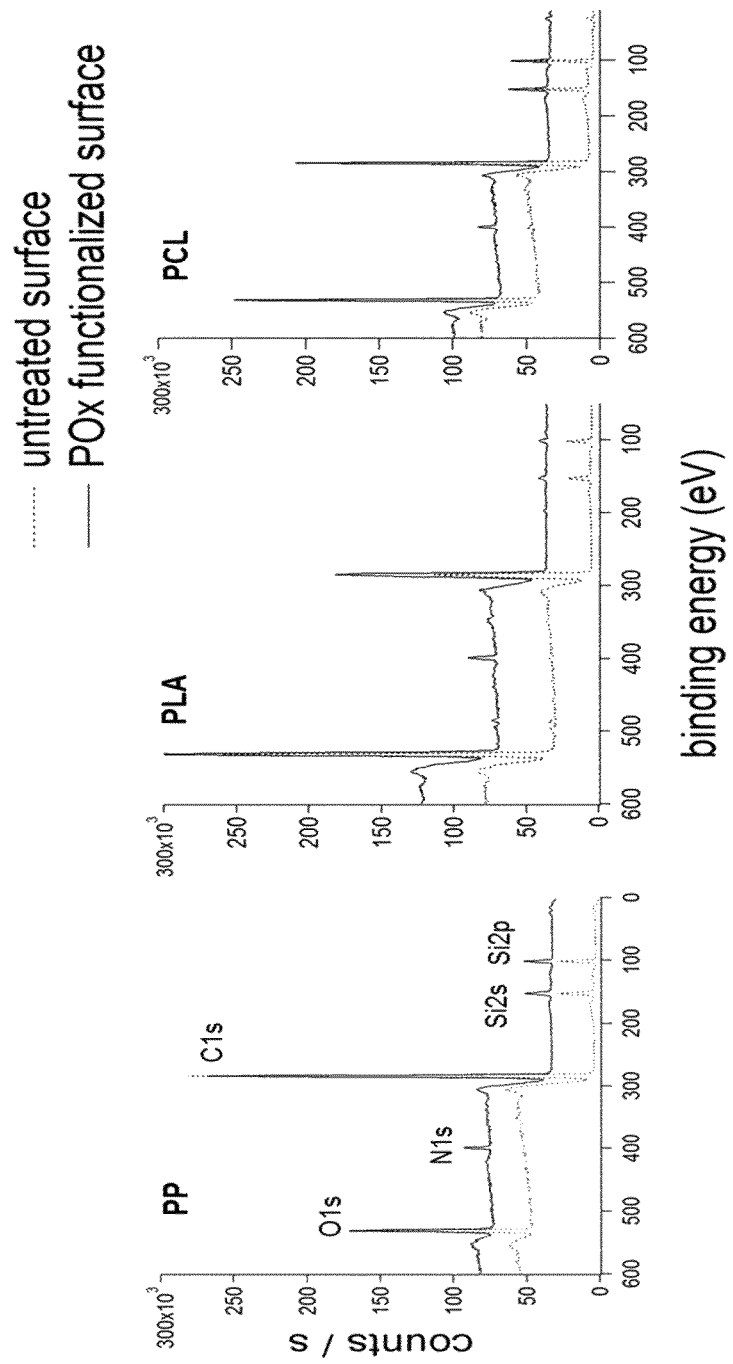
FIG. 11. XPS full spectra of untreated and POx modified polymeric surfaces. Peak assignment is shown exemplarily for the PP samples. Spectra of POx modified surfaces have been offset by 30×10³ counts/s along the y-axis for better visibility.

Surface-Functionalization:

As described in chapter 5. Results are shown in FIG. 11.

Antifouling Effect: Biofilm Formation

*S. epidermidis* ATCC49461 and *E. coli* CFT073 strains were used for these experiments.

Quantification Using Crystal Violet:

The plates are immersed in wells containing the bacterial strain with an OD$_{600}$=0.05, diluted in culture medium. After 72 h incubation at 37° C., the plates are removed from the wells, and vigorously rinsed 3 times with sterile water.

The plates are then placed for 10 minutes in 0.1% crystal violet to stain the bacteria involved in the biofilm. They are then washed 3 times with sterile water to remove excess dye. The bacteria are then precipitated with 250 µl of DMSO. The resulting solution was assayed using a spectrophotometer to measure the OD$_{600}$.

Figure 7:
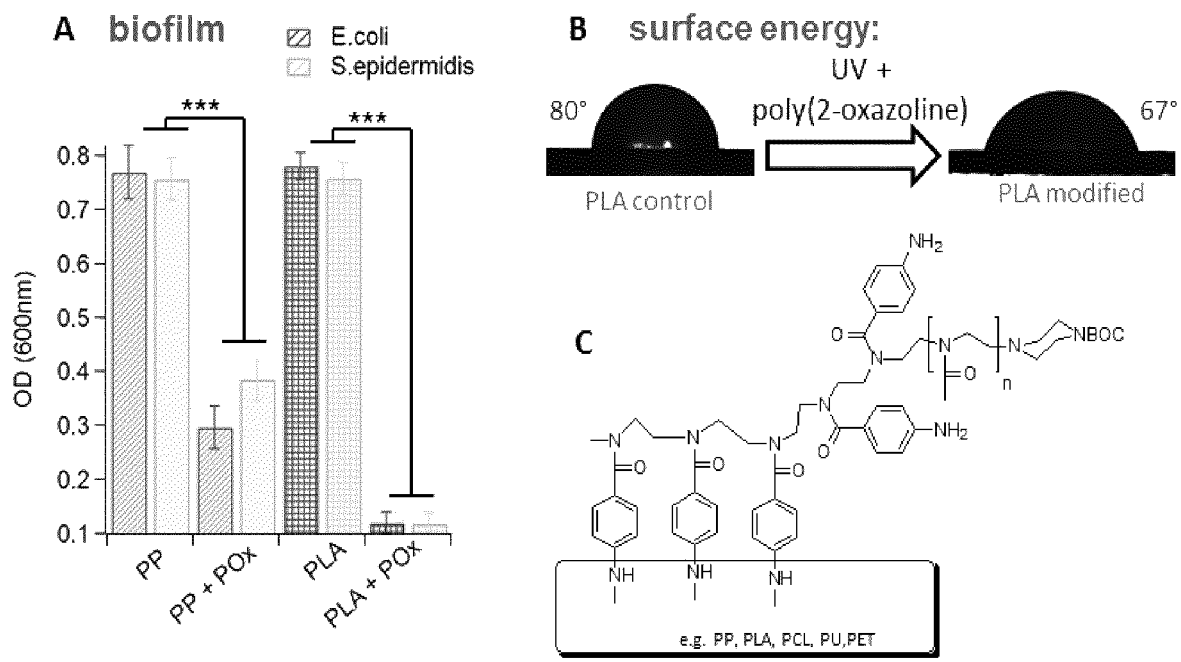
FIG. 7. A: Reduction of biofilm formation on PP and PLA surfaces after UV-functionalization with clip containing poly(2-oxazoline). B: Decrease in contact angle of PLA surface after treatment with poly(2-oxazoline). C: Schematic representation of attachment of (2-methyl-2-oxazoline)-b-poly(2-(4-azidophenyl)-oxazoline) block copolymer on polymer substrate.

A scheme depicting the structure of a surface-modified substrate thus obtained is presented in FIG. 7 (C). FIG. 7 (A) shows the reduction of biofilm formation on such a surface-modified PP and PLA substrate, as compared with a non-grafted control.

Contact Angles

Contact angles were measured via a progressive scan CCD camera (Dataphysics OCAH200) and analyzed using ImageJ software. FIG. 7(B) shows decrease in contact angle of such a surface-modified PLA substrate (B), as compared with an untreated (non-grafted) PLA substrate.

Crystal Violet Assay for Quantification of Submerged Bacterial Biofilms

Material:
Polymer-coated 6-well plate
Tryptic Soy Broth (TSB, Becton-Dickinson)
0.1% Crystal Violet (Carl Roth) in H$_2$O
1×PBS
H$_2$O
33% acetic acid (Carl Roth)
Photometer and single use cuvettes Strain: *Staphylococcus epidermidis* RP62a Setting Bacterial Biofilms.

The bacteria were grown overnight in 2 ml TSB in 13 ml culture tubes at 37° C. shaking with 220 rpm. The absorption of the culture was measured at 600 nm (OD$_{600\ nm}$) and a preculture of 20 ml (in 100 ml flasks) was started with an OD$_{600\ nm}$=0.05 in TSB. The preculture was incubated for 4-6 h at 37° C. shaking with 220 rpm to have a culture in the exponential growth phase. The OD$_{600\ nm}$ was measured and the culture was diluted in TSB to an OD$_{600\ nm}$=0.05. Each well was filled with 4 ml of the bacterial solution. The plate was incubated at 37° C. for 24 h to allow formation of the submerged biofilm.

Staining and Quantification of Biofilms.

Figure 12:
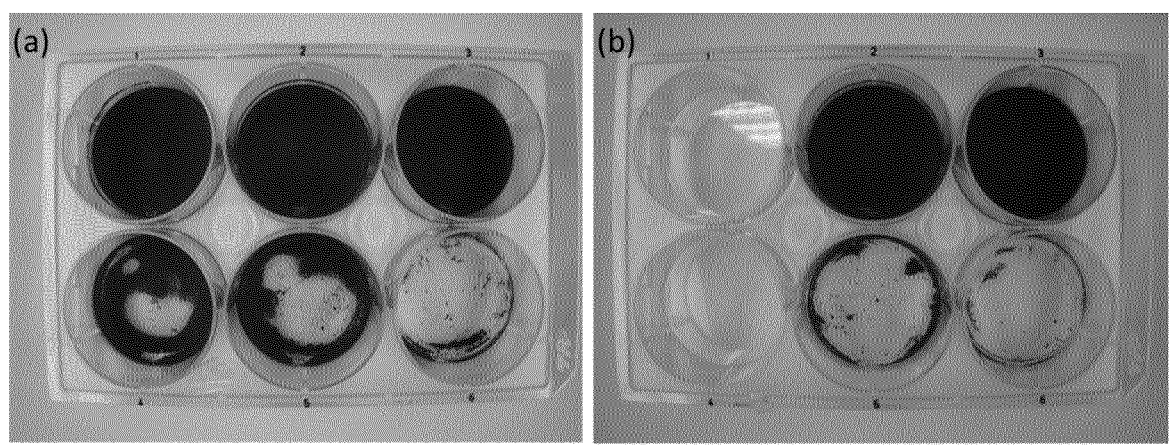
FIG. 12: Biofilm formation of *S. epidermidis* stained with crystal violet on untreated (i.e. not modified) PS (top rows) and on Pox treated (i.e. modified with the polymers described in example 6) PS (bottom rows) with (A) a random copolymer and (B) a gradient copolymer.

The multi-well plate was flipped over to discard the medium. The wells were then gently washed three times with PBS to remove unbound cells. The biofilms were fixed by heating the plate (without the lid) to 65° C. for 30 min. To stain the biofilms, 1 ml 0.1% crystal violet was added to the wells and incubated for 3 min. The dye was discarded and the wells were washed with H$_2$O until no more dye was found in the water (at least 3 times). Results. The obtained results are shown on FIG. 12. It appears that gradient copolymers prevent more efficiently the formation of the biofilm.

7. Functionalization with poly(2-methyl-2-oxazoline)-co-poly(2-(4-azidophenyl)-oxazoline) Copolymers, Rhodamine B Terminated Clip-Synthesis:

2-(4-Azidophenyl)-oxazoline. As Described in Chapter 6.

Poly(2-oxazoline). As Described in Chapter 6.

Poly(2-oxazoline), Rhodamine B Terminated.

1.2 eq Rhodamine B isothiocyanate were dissolved in anhydrous DMF. 1 eq DIPEA and 1 eq poly(2-oxazoline) were added and the reaction mixture was shaken for at least 3 d at 40° C. The crude product was purified via Sephadex LH20 column (MeOH as eluent).

Surface-Functionalization: As Described in Chapter 5.

Fluorescence Measurements

Material.

Leica fluorescence microscope, 20× magnified, green excitation wavelength (555 nm).

Figure 8:
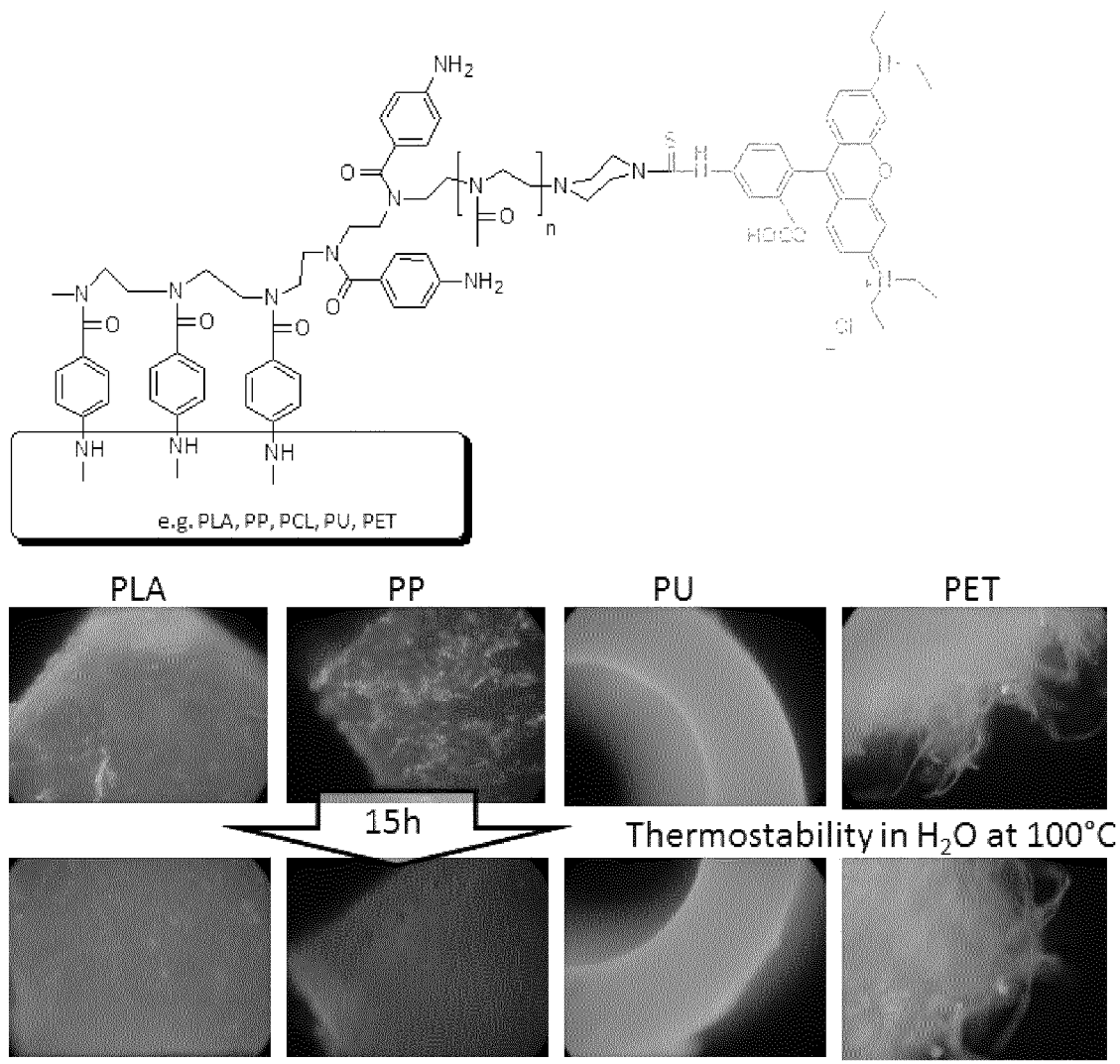
FIG. 8. Top: Scheme of Rhodamine B attached to various polymer surfaces via a clip-containing poly(2-oxazoline) copolymer spacer. Bottom: Fluorescence images of various polymer surfaces modified with the poly(2-oxazoline) copolymer before and after 15 h at 100° C. in $H_2O$.

A scheme depicting the assumed structure of a surface-modified substrate thus obtained is presented in FIG. 8 (A). FIG. 8 also shows fluorescence images of various surface-modified substrates thus obtained, before and after being heated at 100° C. in $H_2O$ for 15 h. These results demonstrate the stability of the surface-modified substrates of the invention.

The invention claimed is:

1. Method for grafting a properties-imparting compound onto a polymeric substrate containing carbon-hydrogen (C—H) bonds, said method comprising:
   a) providing a polymeric substrate;
   b) coating the polymeric substrate with a properties-imparting compound comprising a photoactive aryl-azide moiety of formula (I):

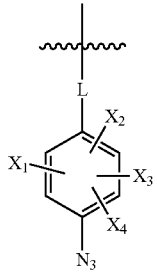

(I)

with $X_1$, $X_2$, $X_3$ and $X_4$ independently representing a hydrogen or a fluorine atom, a $C_1$-$C_6$ alkyl group, $NO_2$ or OH, and L representing NH, —C(O)O—, —S—, —C(O)NH—, —NHC(O)—, —OC(O)—, —NHC(O)NH—, —NHC(S)NH—, —C(O)NRC(O)— with R representing a $C_1$-$C_6$alkyl or triazolyl, so as to obtain a homogeneous dry layer of said properties-imparting compound coated on at least part of the polymeric substrate, and to bring said aryl-azide moiety of formula (I) into covalent bonding proximity with the carbon-hydrogen bonds of the polymeric substrate, provided that when the properties-imparting compound is a polymer, it is a block- or gradient-copolymer with a block or a region rich in repeated units A, said repeated units A comprising the aryl-azide moiety of formula (I) as defined above;

c) irradiating the coated polymeric substrate with a reactive light source, for a time $t_1$ sufficient to form nitrenes that undergo insertion reactions into carbon-hydrogen bonds of the polymeric substrate, $t_1$ being equal to or less than 30 minutes, thereby yielding a grafted polymeric substrate;
   d) optionally washing the obtained grafted polymeric substrate;
   e) repeating steps b), c) and optionally d) at least once; and
   f) optionally drying the grafted polymeric substrate obtained at the end of step e), said properties-imparting compound providing anti-fouling properties, antibacterial properties, or rendering the polymeric substrate radio-opaque or visible in medical imaging; and wherein the method is carried out directly on the polymeric substrate without any prior treatment step.

2. The method of claim 1, wherein the polymeric substrate is a polymeric implantable substrate.

3. The method of claim 1, wherein the polymeric substrate is selected from aliphatic polyesters and copolyesters, copolymers of aliphatic polyesters and polyethers, polycarbonate, polydioxanone, polypropylene, polyethylene, polyethylene terephthalate, polyethylene oxide, polyurea, poloxamer, poloxamine, silicone, polycarboxylate, polyether ether ketone, ABS, Polystyerene, Polyvinylchloride, and polyacrylates.

4. The method of claim 1, wherein the properties-imparting compound is a hydrophilic block-copolymer with a block comprising repeated units A or a gradient-copolymer with a block a region comprising repeated units A, said repeated units A comprising the photoactive aryl-azide moiety of formula (I) as defined in claim 1 with the nitrogen atom covalently bound to the surface of the surface-modified polymeric substrate, said hydrophilic block- or gradient-copolymer imparting anti-fouling properties.

5. The method of claim 4, wherein the hydrophilic block- or gradient-copolymer contains at least repeated units A and B, wherein Repeated units A comprise the photoactive aryl-azide moiety of formula (I) as defined in claim 1, and Repeated units B lack the photoactive aryl-azide moiety of formula (I) as defined in claim 1.

6. The method of claim 5, wherein the molar ratio of repeated units A over repeated units B (repeated units A/repeated units B) is of between 0.01% and 50.

7. The method of claim 4, wherein the hydrophilic block- or gradient-copolymer is a poly(ethylene glycol), a poly(ethylene oxide), a poly((meth)acrylatePEG), poly(($C_1$-$C_6$) alkylamino(meth)acrylate), a linear poly(quaternary ammonium) with a molecular weight of less than 20 000 g·mol$^{-1}$, a zwitterionic poly(betaine), a poly(vinylpyrrolidone), a polylysine, a polyoxazoline, a polyoxazine, a polysarcosine block- or gradient-copolymer or a polyoxazoline-polysarcosine block-copolymer or a polyoxazoline-polyoxazine copolymer.

8. The method of claim 1, wherein the properties-imparting compound is an antibacterial agent selected from:

a polymer selected from: a quaternized poly(vinylpyridine), a quaternized poly(dimethylaminoethylacrylate), a linear quaternized poly(ethyleneimine), a polylysine, a quaternized polylysine, a copolyester of quaternized poly(5-Amino-δ-valerolactone), a quaternized polyoxazoline-polyethyleneimine copolymer, wherein the quaternized polymers are quaternized with a $C_3$-$C_{15}$ alkyl, a quaternary ammonium of formula (IIa):

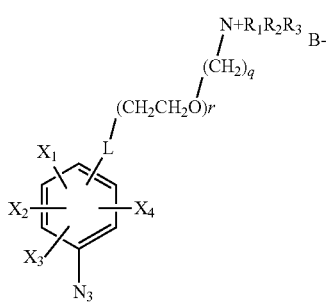

with $X_1$ to $X_4$ and L as defined above,
q an integer from between 0 and 10,
r an integer from between 0 and 3000, and $R^1$ and $R^2$ each independently selected from a hydrogen atom or a $C_1$-$C_6$ alkyl group, $R^3$ independently selected from a hydrogen atom or a $C_1$-$C_9$ alkyl group and B— representing a pharmaceutically acceptable anion;
a quaternary phosphonium of formula (IIb):

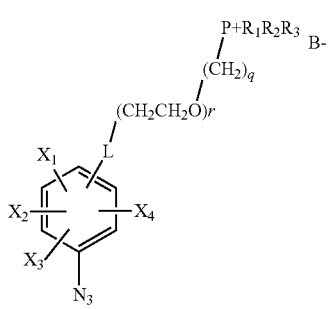

with $X_1$ to $X_4$ and L as defined above,
q an integer from between 0 and 10, r an integer from between 0 and 3000,
$R^1$, $R^2$ each independently selected from a hydrogen atom or a $C_1$-$C_6$ alkyl group, $R^3$ independently selected from a hydrogen atom or a $C_1$-$C_9$ alkyl group, and B— representing a pharmaceutically acceptable anion;
a quaternary pyridinium of formula (IIc)

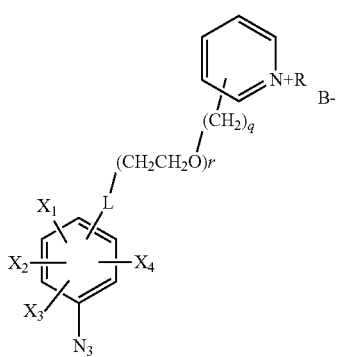

with $X_1$ to $X_4$ and L as defined above, q an integer from between 0 and 10, r an integer from between 0 and 3000, R selected from a hydrogen atom or a $C_1$-$C_9$ alkyl group, and B— representing a pharmaceutically acceptable anion;

an antibacterial peptide of 25 amino-acids or less, comprising a pending group of formula (I) as defined in claim 1.

9. The method of claim 1, wherein the properties-imparting compound is a radio-opaque iodinated contrast agent, a gadolinium complex, a fluorescent compound, or a near-infrared fluorescent compound.

10. The method of claim 9, wherein the properties-imparting compound comprises a gadolinium complex of DOTA (1,4,7,10-tetraazacyclododecan-1,4,7,10-tetraacetic acid), DTPA (diethylenetriaminopentaacetic acid), DO3A (1,4,7,10-tetraazacyclododecan-1,4,7-triacetic acid), HPDO3A (10-(2-hydroxypropyl)-1,4,7,10-tetraazacyclododecan-1,4,7-triacetic acid), TRITA (1,4,7,10-Tetrakis(carboxymethyl)-1,4,7,10-tetraazacyclotridecane), TETA (1,4,8,11-Tetrakis(carboxymethyl)-1,4,8,11-Tetraazacyclotetradecane), BOPTA (4-carboxy-5,8,11-tris(carboxymethyl)-1-phenyl-2-oxa-5,8,11-triazatridecan-13-oic acid), NOTA (1,4,7-triazacyclononane-N,N',N44-triacetic acid), PCTA (3,6,9,15-tetraazabicyclo[9.3.1]pentadeca-1(15),11,13-triene-3,6,9-triacetic acid), DOTMA ((alpha, alpha', alpha'', alpha''')-tetramethyl-1,4,7,10-tetraazacyclododecan-1,4,7,10-tetraacetic acid), AAZTA (6-amino-6-methylperhydro-1,4-diazepinetetraacetic acid) and HOPO (1-hydroxypyridin-2-one).

11. The method of claim 9, wherein the properties-imparting compound is:

an iodinated compound of formula (III):

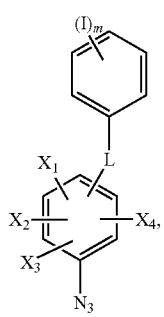

with $X_1$ to $X_4$ and L as defined in claim 1 and m representing 1, 2, 3 or 4, or a polymer comprising an iodinated moiety of formula

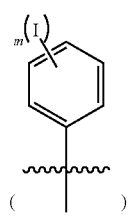

with m representing 1, 2, 3 or 4.

12. The method of claim 9, wherein the properties-imparting compound is:

a rhodamine derivative of formula (Va):

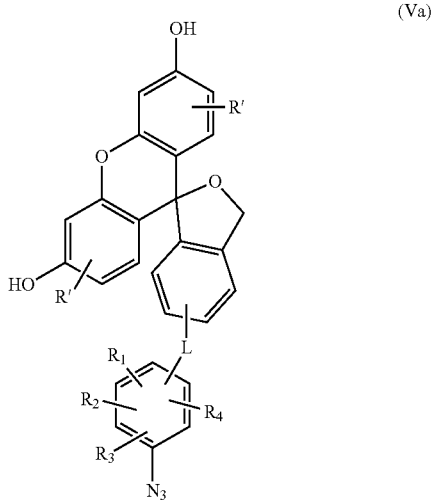

(Va)

with $X_1$ to $X_4$ and L as defined in claim 1, $R^1$, $R^2$, $R^3$ and $R^4$ each independently selected from a hydrogen atom or a $C_1$-$C_6$ alkyl group, and $R^5$ selected from a hydrogen atom, a COOH or a C(O)O$C_1$-$C_6$ alkyl group;

a cyanin derivative of formula (Vb):

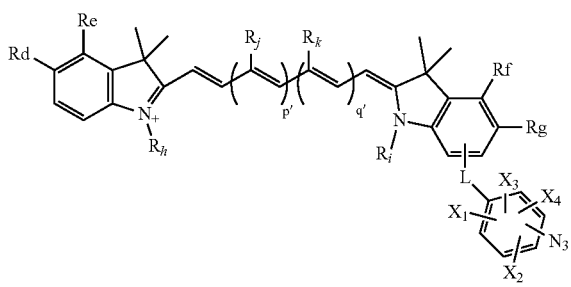

(Vb)

with $X_1$ to $X_4$ and L as defined in claim 1, p' being 0 or 1, q' being 0 or 1 if p' is 0 then $R_k$ is H, if q' is 0 then $R_j$ is H, if p' is 1 and q' is 1, then $R_j$ and $R_k$ are both H or taken together, form a-$CH_2CH_2CH_2$— bridging group, $R_d$ is selected from H and $SO_3Na$, and $R_e$ is H or taken together, $R_d$ and $R_e$ form a-$CH_2CH_2CH_2$- or CHCHCH— bridging group, $R_g$ is selected from H and $SO_3Na$, and $R_f$ is H, or taken together, $R_f$ and $R_g$ form a-$CH_2CH_2CH_2$- or CHCHCH— bridging group, $R_h$ being selected from a ($C_1$-$C_6$)alkyl group, optionally substituted with a $SO_3$- or a COOH group, $R_i$ being selected from a ($C_1$-$C_6$)alkyl group, optionally substituted with a $SO_3Na$ or a COOH group, or a fluorescein derivative of formula (Vc):

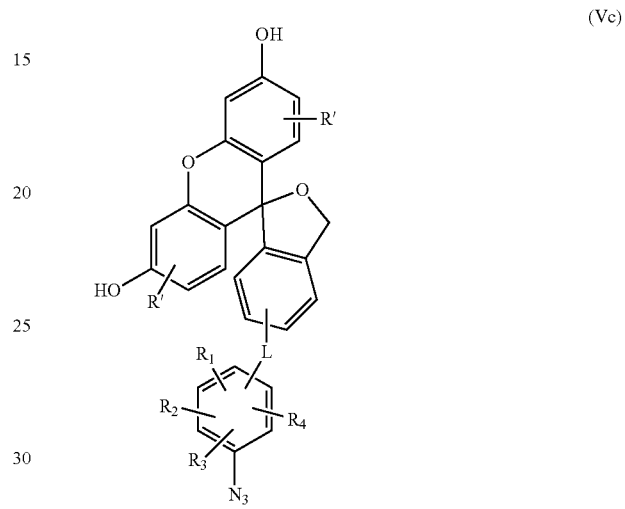

(Vc)

with $X_1$ to $X_4$ and L as defined in claim 1, and R' representing H, or a-$CH_2CH_2COOH$ or —CH=CHCOOH group.

13. The method of claim 2, wherein the properties-imparting compound is a hydrophilic block copolymer with a block comprising repeated units A or a gradient-copolymer with a block a region in comprising repeated units A, said repeated units A comprising the photoactive aryl-azide moiety of formula (I) as defined in claim 1 with the nitrogen atom covalently bound to the surface of the surface-modified polymeric substrate, said hydrophilic block- or gradient-copolymer imparting anti-fouling properties.

14. The method of claim 3, wherein the properties-imparting compound is a hydrophilic block copolymer with a block comprising repeated units A or a gradient-copolymer with a block a region in comprising repeated units A, said repeated units A comprising the photoactive aryl-azide moiety of formula (I) as defined in claim 1 with the nitrogen atom covalently bound to the surface of the surface-modified polymeric substrate, said hydrophilic block- or gradient-copolymer imparting anti-fouling properties.

* * * * *